(12) United States Patent
Kronberg

(10) Patent No.: US 6,321,119 B1
(45) Date of Patent: Nov. 20, 2001

(54) PULSED SIGNAL GENERATOR FOR BIOELECTRIC STIMULATION AND HEALING ACCELERATION

(75) Inventor: James W. Kronberg, Aiken, SC (US)

(73) Assignee: Healthonics, Inc., Aiken, SC (US)

( * ) Notice: Subject to any disclaimer, the term of this patent is extended or adjusted under 35 U.S.C. 154(b) by 0 days.

(21) Appl. No.: 09/478,103

(22) Filed: Jan. 4, 2000

Related U.S. Application Data

(63) Continuation-in-part of application No. 09/159,978, filed on Sep. 24, 1998, now Pat. No. 6,011,994.
(60) Provisional application No. 60/059,880, filed on Sep. 24, 1997.

(51) Int. Cl.$^7$ ........................................................ A61N 1/08
(52) U.S. Cl. .................................................................. 607/66
(58) Field of Search ................................. 607/66, 69, 76, 607/72

(56) References Cited

U.S. PATENT DOCUMENTS 5,217,009 * 6/1993 Kronberg .
5,413,596 * 5/1995 Kronberg .

OTHER PUBLICATIONS

R.B. Borgens, "New Horizons in the Treatment of Spinal Cord Injury," by the Center for Paralysis Research, School of Veterinary Medicine, Purdue University, (Sep. 25, 1998).*

R.E. Shupe, et al., "The Friendly Fields of RF," IEEE Spectrum, vol. 22, No. 6 (Jun., 1985), pp. 66–71.*

J.D. Zoltan, "Electrical Stimulation of Bone: an Overview," Seminars in Orthopaedics, vol. 1, No. 4 (Dec. 1986), pp. 242–252.*

* cited by examiner

*Primary Examiner*—Scott M. Getzow
(74) *Attorney, Agent, or Firm*—Maria Reichmanis

(57) ABSTRACT

A pulsed signal generator for biomedical applications, including electrical stimulation of fracture healing, treatment of osteoporosis, strengthening of freshly-healed bone after removal of a cast or other fixation device, and iontophoresis. The generator includes dual asymmetric oscillators and associated circuitry to deliver signals efficiently throughout the area to be treated. The components of the generator are selected so as to produce any desired output signal, including fixed and variable amplitude, fixed, variable, and swept frequency signals, and optional DC biasing. The pulse frequency and/or interval can be fixed or adjustable. In a preferred embodiment of the invention, the generator is powered by readily-available, inexpensive batteries.

28 Claims, 9 Drawing Sheets

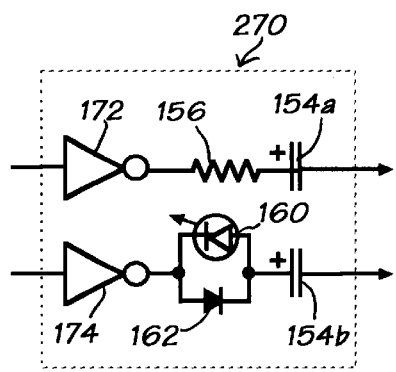
Fig. 13
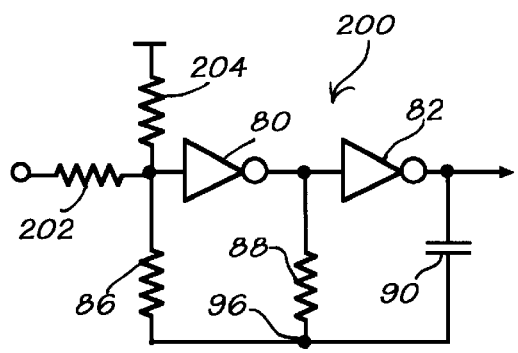
Fig. 14A
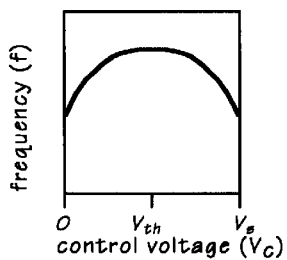 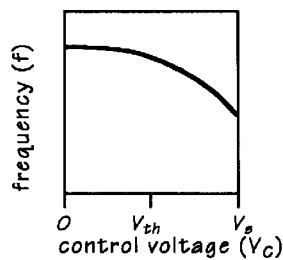 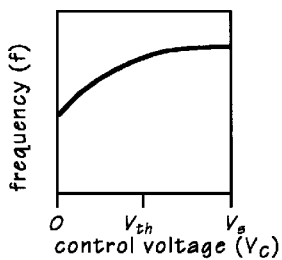 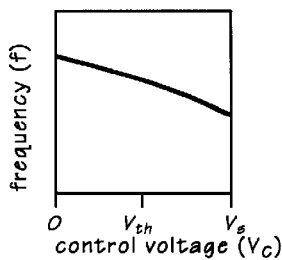
Fig. 14B    Fig. 14C    Fig. 14D    Fig. 14E
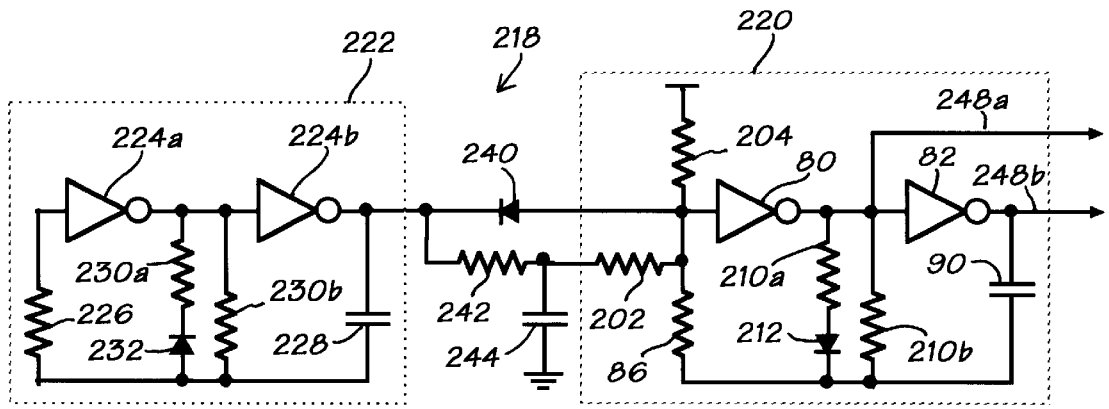
Fig. 15A

PULSED SIGNAL GENERATOR FOR BIOELECTRIC STIMULATION AND HEALING ACCELERATION

This application is a continuation-in-part of application Ser. No. 09/159,978 filed on Sep. 24, 1998, now U.S. Pat. No. 6,011,994, which claims benefit of Prov. No. 60/059,880 field Sep. 24, 1997.

BACKGROUND OF THE INVENTION

1. Field of the Invention

The present invention relates to a pulsed signal generator for biomedical applications. In particular, the present invention relates to a simple, compact pulsed signal generator with an optional superimposed DC bias signal, for use in stimulation of fracture healing, treatment of osteoporosis, and other applications.

2. Discussion of Background

Several million Americans suffer broken bones every year; many of them having multiple fractures. Bone fractures are a major source of pain, inconvenience, expense, lost time and diminished workplace productivity. Even in a young, healthy patient, many fractures must be immobilized for six weeks or longer while healing takes place; after the cast or other fixation device is removed, the patient's activities must be restricted until the newly-healed bone regains its full strength. In the elderly population and in persons with poor health, malnutrition, or medical conditions such as diabetes that impact normal healing processes, fractures may heal slowly or not at all resulting in what are known as "nonunions."

Fracture healing, and in many cases the healing of other tissues as well, can be accelerated by the application of suitably-chosen, low-level electrical signals resembling those naturally present in tissues subjected to normal environmental levels of mechanical stress. Typical methods of doing this, however, require apparatus which is expensive, bulky and inconvenient to use, and/or requires surgical implantation.

Human bone is a combination of organic and mineral components. The chief mineral constituent of bone is hydroxyapatite, a complex calcium phosphate ($Ca_5(PO_4)_3OH$) in crystalline form. Like quartz, hydroxyapatite is piezoelectric: that is, it generates an electric charge or current when mechanically stressed. Collagen, the tough fibrous protein which surrounds the hydroxyapatite crystals and binds them together, is also piezoelectric.

Normally the electric signals generated by bone (sometimes called "bone talk") are weak and of relatively low frequency, replicating the pattern of mechanical forces placed on the bones from outside. When bone is strongly stressed, however, the hydroxyapatite crystals eventually start to slip little by little past each other and higher-frequency signals, having a characteristic pattern of sharp pulses separated by intervals of no signal, begin to appear. These signals arise from a mechanism much like that which creates the noise of a creaking floor: the wood surfaces or fibers alternately stick together and then, when the applied force becomes too great, give way abruptly and create a pulse of sound. Many such pulses in rapid succession make up the sound we hear when walking across a creaking floor. A sensitive microphone can pick up the audio signals emitted by stressed bone; since any piezoelectric material is itself a microphone of sorts, the same pattern also appears as an electrical signal.

Osteoblasts, the cells within bone which secrete and deposit hydroxyapatite, are very sensitive to electric signals of this type and respond by forming larger amounts of hydroxyapatite. This creates a feedback mechanism, causing the bone to be strengthened automatically at points of stress concentration where the signals tend to be strongest. When the feedback loop breaks down—as when the bone receives little stress, when the diet is calcium-deficient, or when disease makes the cells less sensitive—osteoporosis can result. By the same token, restoring or strengthening the "bone talk" electrical signals can reverse or prevent the condition.

When a bone is fractured, current medical practice is first to "set" the bone with the fractured end surfaces close together, and then to immobilize it with a cast, splint, or fixator (internal or external) until the fracture heals. This practice has advantages and disadvantages. One advantage is that, since the fractured surfaces are close together, little bone tissue is needed to close the gap. On the other hand, the immobilized section of bone is exposed to little or no stress, next to no "bone talk" is generated, and thus, once again, the feedback loop which governs formation of new bone is broken. As a result, the osteoblasts in the vicinity of the fracture work at reduced capacity and the fracture takes a long time to heal. In all too many cases, complete healing never takes place and the fracture becomes a permanent nonunion.

It has long been known that the application of electric currents can restore healing (of nonunions) and speed bone growth and repair (of normal fractures). In the mid-1960s, C. A. L. Bassett and others measured the weak electrical signals generated by bone itself, analyzed and reproduced those signals artificially, and used them to reverse osteoporosis or aid in the healing of fractured bones.

A waveform which has been found effective is shown schematically in FIG. 1, where a line 10 represents the waveform on a short time scale, a line 12 represents the same waveform on a longer time scale, an interval 14 represents a peak voltage or current amplitude, and intervals 16, 18, 20, and 22 represent the timing between specific transitions. Alternate repetition of intervals 16 and 18 generates pulse bursts 24, each having a length 20 and separated by an interval 22 wherein the signal undergoes no transitions. For example, interval 16 may be about 200 microseconds, interval 18 about 28 microseconds, interval 20 about 5 milliseconds, and interval 22 about 62 milliseconds so that pulse bursts 24 recur at a frequency of about 15 Hertz.

The precise characteristics of the signal depicted in FIG. 1 are not at all critical. Indeed, the characteristics of naturally-occurring bone electrical signals depend on several factors, including the type, size and mineral density of the bone involved, the amount of stress and its rate of application, and probably on many other factors as well. Hence, osteoblasts are believed to be able to respond to a wide range of electrical signals. Typical laboratory studies of the effects of applied electrical signals on bone growth have been performed using signals that are approximately of the form shown in FIG. 1, with intervals 16, 18, 20 and 22 each within about a factor of five (i.e., from about 20% to about 500%) of the values given above. Some studies have utilized continuous pulse trains where interval 18 is reduced to zero. For example, a continuous pulse train 26 is shown in FIG. 2, may have an interval 20 of about 380 microseconds and an interval 22 of about 13 milliseconds, for a repetition rate of 75 Hertz (FIG. 2). Signals such as pulse train 26 have been used widely and successfully in treating osteoporosis.

While it was initially thought that signals applied from outside the body would have to be relatively strong to be biologically active, it now appears that a threshold effect is involved. Signals at levels comparable to those of normal "bone talk" (that is, resembling the signal shown in FIG. 1 with interval 14 representing a few microamperes per square centimeter of tissue cross-section) can increase the rate of healing in fresh fractures by as much as 100% and can restimulate healing in up to 80% of long-standing nonunions. Surprisingly, signals of like form but greater amplitude (as much as thousands of times more powerful) provide no greater benefit than the weaker signals, and often less. This relationship is shown in FIG. 3, where a line 28 represents the level of benefit at various signal intensities, where "benefit" refers to observable increases in healing (or normal fractures) or stimulation of healing (of nonunions). A peak applied voltage 30 typically falls somewhere around ten microamperes per square centimeter, and a crossover point 32 at about a hundred times this value. Beyond point 32, the signal slows healing rates rather than increasing them, and may itself cause further injury.

Healing is a cellular process triggered by the occurrence of an injury (for purposes of this specification, the terms "wound" and "injury" refer to tissue damage or loss of any kind, including but not limited to cuts, incisions, abrasions, lacerations, fractures, contusions, burns, and so forth). In general, the progress of healing in any injured tissue, whether bone or a soft tissue such as skin or muscle, takes place in several well-defined stages of cell migration and proliferation. These are shown schematically in FIG. 4. Here, lines 40 through 44 represent the populations of various cell types involved in repair, while lines 46 and 48 show the progress of the repair through tissue rebuilding.

Neutrophils and monocytes, indicated by lines 40 and 42, respectively, are elements of the immune system which clean away damaged cells and destroy foreign organisms such as bacteria (if present) at the injury site. Their activity, which typically peaks from the second to the fourth day after the injury, corresponds to the inflammation phase of healing.

Fibroblasts, another type of cell indicated by line 44, then begin the repair process proper: building a framework of collagen, the same tough protein which binds the mineral components of bone together, and to which other cell types then adhere to form the rebuilt tissue. At about the same time, the number of capillaries, indicated by line 46, increases to supply needed materials for tissue rebuilding. The fibroblast population usually peaks around the sixth day after the injury, when the most rapid collagen formation is taking place (as shown by line 48). Once the basic framework is laid down, typically around the eighth day after the injury, the fibroblast population decreases. Collagen is deposited at a slower rate for several weeks more, while other types of cells continue to migrate into the injury site and proliferate to form a complete tissue.

Increases in the rate of healing have also been observed in soft-tissue injuries, such as nerve damage and skin wounds, when electrical signals were applied experimentally to the injured tissue or were being used to treat nearby bone. Hence, it seems likely that healing processes are naturally stimulated by "bone talk"-type electrical signals or by the piezoelectric response of other body tissues to environmental stress.

EXAMPLE 1

A volunteer patient was treated with a Bassett-type pulsed waveform in the spring of 1997. The patient had suffered three accidental abrasions on the dorsal surface of one hand; the abrasions were of approximately equal surface area. One abraded area (initially, slightly the worst of the three) was treated by application of a pulsed waveform of approximately 50 $\mu A/cm^2$; the second area was covered with electrode material but otherwise untreated; the third area was untreated. Results indicated that application of pulsed electrical stimulation roughly quadrupled the rates of the early healing stages compared to the covered and untreated areas. Inflammation in the treated abrasion was initially more severe than in the others; however, this phase of the healing process was completed much more quickly. After two days of intermittent treatment (two approximately 8-hour treatments on successive nights during sleep), the inflammation had almost completely subsided and a collagen framework for the new skin was already in place. This stage would normally not have been reached until about the eighth day post-injury.

Patients treated with the above-described types of pulsed signals often report quick relief from the pain accompanying fractured bones and traumatized soft tissues. The mechanism by which this occurs may be similar to the one used in TENS (transcutaneous electric nerve stimulation), in which repeated electric pulses applied to a nerve, themselves so weak as to be imperceptible, can nevertheless block the transmission of pain signals to the brain.

Nerves respond to electrical stimuli not only by ceasing to transmit pain messages, but also, in at least some types of injury, by regenerating with increased speed. This effect has been demonstrated in a number of studies, including those conducted by Richard Borgens at the Purdue University School of Veterinary Medicine. Borgens reports that application of weak, oscillating electrical current across the site of an accidental spinal cord injury in a paraplegic dog can modify the growth and regeneration of damaged nerve fibers. In Example 1 above, the patient reported that sensation in the treated area had returned to essentially normal after approximately 48 hours of intermittent treatment.

Electrical stimulation can also produce a wide range of responses in other body systems. The frequency and timing of the signal waveform appears to have some bearing on which of these are more affected. It appears possible that appropriately-designed waveforms may prove useful for stimulating muscles, such as those in fractured and immobilized limbs or those of temporarily paralyzed persons, to help prevent atrophy and preserve muscle tone. Other applications may include stimulation of the endocrine glands and the immune system. For example, autoimmune conditions such as arthritis may be susceptible to localized, bioelectric immunosuppression without affecting the ability of the body as a whole to throw off infection. Much more research will be needed in order to evaluate the potential of such effects in healing or in the treatment of diseases, and to determine the optimum waveform for each application.

Traditional Western medicine has accepted the efficacy of electrical stimulation only grudgingly, and despite its great healing potential it has so far been used only rarely. This may be a legacy from an early, widely-accepted hypothesis that electrical signals must have high intensities to be biologically effective, and that any effects are due solely to tissue heating. As a result, most presently-available devices rely either on direct implantation (of electrodes or of entire electronic packages) or on inductive coupling through the skin. The need for surgery and biocompatible materials in the one case, and excessive circuit complexity in the other, has kept the price of these devices very high, in the range of several thousands to tens of thousands of dollars each. Inductive coupling is also very inefficient, so that signals must originally be generated at hundreds or thousands of times the desired power level; hence the generators must either be plugged into a wall outlet during operation or require the user to carry around heavy, cumbersome battery packs. Only in the realm of TENS does it seem to have been widely realized that biologically effective signal levels can simply be transmitted through the skin, using self-adhesive electrodes, with minimal power loss.

Many different bone-growth stimulators are available, including those described in U.S. Pat. Nos. 5,217,009 and 5,413,596, the disclosures of which are incorporated herein by reference. The former design offers several advantages, including relatively low cost and light weight. However, it uses linear, analog timing integrated circuits with relatively high supply-current demand, requiring frequent battery changes while the device is in use.

The circuits of U.S. Pat. Nos. 5,217,009 and 5,413,596 are shown in block form in FIGS. 5A and 5B, as circuits 60 and 68, respectively. Circuit 60 includes two integrated timing circuits 64a, 64b and a logic section 66 (FIG. 5A). Circuit 68, described in U.S. Pat. No. 5,413,596, eliminates the timing circuits, but at the cost of much greater circuit complexity involving a clock oscillator 70 driving a binary divider chain 72 with multiple outputs to a logic section 74.

An often-overlooked concern in the area of electrical stimulation is that of habituation: over time, living organisms (including humans) show diminishing sensitivity to stimuli which remain relatively unchanging. Human hearing provides a familiar example: although a steady sound such as a car engine is very evident at first, the ear eventually becomes accustomed to the sound so that, after a period of time, the sound is hardly noticeable. If, however, the sound changes, it will again be noticed. This phenomenon is the basis for beeping or warbling alarms, and why, to an experienced driver, the first sign of engine trouble is often a slight change in the otherwise almost unnoticed noise of the vehicle. By the same token, body cells may become habituated to a particular electrical stimulus and begin to respond to it less effectively.

Another concern is expressed by the biological axiom, "populations are diverse": no two members of a given population, whether of human beings or of single cells, are ever exactly alike. Thus, some cells of a type that respond in a given way to a particular type of signal may react more strongly to frequencies slightly higher, and others to frequencies slightly lower, than the average. If the signal presented to the cells contains many such frequencies, therefore, the response of the tissue as a whole may be significantly greater than if a single frequency were used.

It is believed that habituation effects and population diversity at least partly explain why AC (i.e., alternating current) signals usually work better in electrotherapy than DC (direct current) signals, and why pulse bursts may be more effective than single pulses. Indeed, studies on electrical stimulation of bone growth have shown that application of DC stimuli alone is problematic in stimulating bone regeneration since bone grows near the cathode (i.e, the negative electrode) but often dies away near the anode. This phenomenon may result from electrolytic effects, which can cause tissue damage or cell death through pH changes or the dissolution of toxic metals into body fluids. For this reason, many bioelectronic bone growth stimulators rely solely on AC effects, removing any net DC current from the outputs by passing the signal through a blocking capacitor. Such a capacitor forces the positive and negative output currents, when summed over a full cycle of the output waveform, to be equal, canceling each other out.

On the other hand, iontophoretic (i.e., DC) techniques are usefull in many medical applications, for example, delivery of electrically-generated silver ions which inhibit bacterial and fungal growth. Iontophoresis may also be carried out using water-soluble, bioactive ionic substances, thus, antibiotics and other medications with water-soluble forms can be delivered via iontophoresis. For example, most alkaloids take on an extra proton per molecule in water solution, thereby becoming positive ions which can be transported into the body by DC electricity. This class of compounds includes a large fraction, if not the majority, of both naturally-derived and synthetic medications of all kinds. Unfortunately, conventional iontophoretic devices cannot be used in combination with AC waveform generators, since these types of devices include diodes (or other circuitry) which could short out the positive portion of the waveform.

An ideal bioelectric signal generator for medical applications (including but not limited to bone repair and other healing applications) would be lightweight, compact, fully self-contained, inexpensive to build and maintain, safe for unsupervised home use by patients, and require no external coils or battery pack. The signal generator should be capable of being taped directly to an arm or leg cast, affixed to an athletic brace or external fixation device, fastened to a patient's arm or leg by VELCRO straps or other convenient means, or even simply be carried in the user's pocket, depending upon the condition to be treated and its location. Signals such as those described above, or alternatively signals of the same general form but with other timing characteristics, could be selected either by a suitable choice of components, or simply by turning a dial to select one of a plurality of available signals. Preferably, such a device would generate low-power, pulsed waveforms with high efficiency (and thus low battery drain) using only readily-available, lowcost circuit components. Most preferably, such a device would be able to generate waveforms having a very wide achievable range of timing intervals, with or without a superimposed DC component, so as to address habituation effects, variations in patient sensitivity and response, and a diverse range of applications.

SUMMARY OF THE INVENTION

According to its major aspects and broadly stated, the present invention is a portable, battery-powered signal generator for biomedical applications. The generator, which is capable of generating the above-described "Bassett-type" waveforms either with or without a superimposed DC bias voltage, includes dual asymmetric oscillators and associated circuitry that, in combination, deliver a user-selected electrical signal efficiently throughout the area to be treated. The output signal of the generator is either fixed or variable, depending on the selection of components. The generator is light in weight, thus, it can be attached to a cast without any great increase in either weight or bulk. It is compact, self-contained, and can be taped to a cast, attached to an external fixation device, brace, or the like, or fastened to a patient's body by any convenient means. It can be used for a variety of biomedical applications, including but not limited to stimulation of healing in nonunions, acceleration of normal healing, treatment of osteoporosis, or to strengthen a freshly-healed bone after a cast or other fixation device has been removed. The optional DC component, either alone or in conjunction with a pulsed output signal, allows for the administration of medicaments via iontophoresis.

An important feature of the present invention is the provision for superimposing a positive or negative DC component on a selected type of AC output signal (fixed or variable frequency, swept frequency, etc.). This feature allows for the administration of iontophoretic treatment (for example, to deliver silver ions for prophylactic or therapeutic treatment of localized infections) simultaneously with pulsed signals such as those used for electrical stimulation of fracture healing, through the same electrodes and with the same unit.

Another important feature of the present invention is the use of swept-frequency signals for stimulation of fracture healing and like applications. While swept-frequency techniques are used in TENS (transcutaneous electric nerve stimulation) for the relief of pain, it is believed that these techniques have not heretofore been used for stimulation of bone growth and other healing applications. In particular, no known device is capable of generating swept-frequency signals in combination with controlled DC signals, in a small, lightweight, and compact unit. While not wishing to be bound by theory, it is believed that such swept-frequency electrical signals are biomedically analogous to strobe lights and "beeping" or "warbling" audio alarms, in that these types of signals are less likely to lead to habituation effects and resulting decreases in effectiveness.

Another feature of the present invention is the use of dual asymmetric oscillator circuits to generate waveforms that can be combined to produce an output waveform having virtually any desired characteristics. In one preferred embodiment of the invention, one of two asymmetric oscillators is controlled by the other: that is, the output of the second oscillator is "on" or "off" depending on whether the output of the first oscillator is "low" or "high," respectively. Surprisingly, the combination of a relatively simple asymmetrical resistive element or resistive network with a normally symmetrical oscillator circuit can create a circuit that generates an output signal whose characteristics—frequency, duty cycle, amplitude—can be determined over a wide range by the particular selection of components. Thus, two such circuits with output signals having appropriately-selected characteristics can be combined to produce the desired output waveform with a surprisingly simple overall circuit configuration. In another preferred embodiment, either or both of the asymmetric oscillator circuits may be replaced by suitable conventional integrated circuit devices without significantly affecting the operation of the invention.

Still another feature of the present invention is the use of simple, inexpensive, readily-available components to produce the desired output signal, whether a "Bassett-type" signal or—by a suitable selection of components—some other biologically active signal (or combination of signals) that has a desired effect. Indeed, many of the components of the generator can be fabricated on a single logic chip, resulting in small size and cost-effective assembly.

Yet another feature of the present invention is the use of conventional, readily-available low-voltage batteries as a power source for the generator. This feature reduces the size and weight of the generator, and adds to its safety and ease of use for a patient undergoing treatment. Typically, the batteries need to be replaced at infrequent intervals (generally no more than once per week or even less often, depending on the output signal and the particular application), simplifying patient compliance and reducing cost. The possibility of electrical injuries is greatly reduced, since the generator is not connected to AC line current during use, does not produce high voltages, and does not generate frequencies likely to induce ventricular fibrillation. Because of the above-noted threshold effect, only low power levels are required to produce therapeutic effects; thus, the generator cannot produce an electrical shock hazard even in the event of a malfunction. Thus, the invention is suitable for unsupervised home use.

Another feature of the present invention is its versatility. The components of the generator can readily be selected so as to produce any desired output waveform, including fixed-magnitude signals and (via suitable voltage-regulating devices) variable-magnitude signals, fixed frequency profiles, swept frequency profiles, and DC-biased output signals, separately or combined. In addition, the pulse frequency, pulse interval, and (if desired) pulse duty cycle can be fixed or adjustable, as may be convenient. It will be apparent that a generator having an adjustable output signal is useful for a greater variety of applications than one having a fixed output; on the other hand, medical professionals may prefer a generator having a fixed output, or an output that is adjustable only in magnitude, for outpatient use by their patients. In one embodiment of the invention, the user can select a signal for a given application by turning a dial or using a keypad to select one of a plurality of available signals. In another embodiment, the generator has complementary outputs (that is, the output waveform at one such output is equal to that at the other but of opposite polarity). Complementary outputs double the effective output voltage of the generator: a higher voltage not only yields greater flexibility in treatment options, but more easily permits a "swamping" resistor to be added in series with the output in order to minimize the effects of the resistance of intact skin.

Still another feature of the present invention is the use of standard, readily-available TENS-type electrodes to deliver the biologically-effective signal. No special training is required to use these types of electrodes; prescribed treatment can be continuous, thereby minimizing problems related to patient compliance.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIGS. 11–13 are circuit diagrams of additional signal generators according to the invention;

FIG. 14A is a circuit diagram of a swept-frequency signal generator according to a preferred embodiment of the present invention;

FIGS. 14B–E illustrate the operation of the generator of FIG. 14A;

FIG. 15A shows another swept-frequency signal generator according to the invention;

DETAILED DESCRIPTION OF PREFERRED EMBODIMENTS

Figure 1:
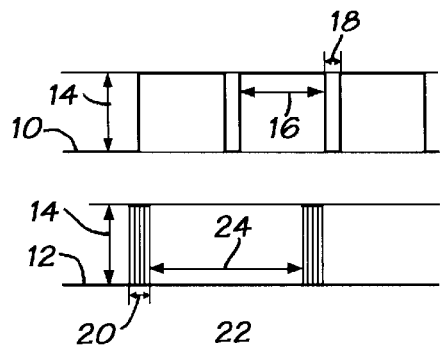
FIG. 1 shows a waveform used for the stimulation of fracture healing.

In the following detailed description, reference numerals are used to identify structural elements, portions of elements, surfaces and areas in the drawings. It should be understood that like reference numerals are intended to identify the same structural elements, portions or surfaces consistently throughout the several drawing figures, as such elements, portions or surfaces may be further described or explained by the entire written specification. As used in the following description, the terms "horizontal," "vertical," "left," right," "up," "down," as well as adjectival and adverbial derivatives thereof (e.g., "horizontally," "rightwardly," "upwardly," etc.) refer to the relative orientation of the illustrated structure as the particular drawing figure faces the reader. Similarly, the terms "inwardly" and "outwardly" refer to the orientation of a surface of revolution relative to its axis.

Figure 6:
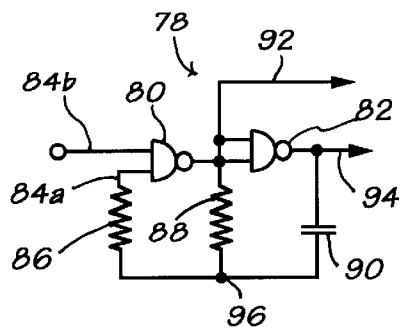
FIG. 6 is a circuit diagram of an oscillator circuit.

Referring now to FIG. 6, there is shown an oscillator circuit 78 that is widely used as a clock in CMOS (i.e., complementary metal oxide semiconductor) circuits where frequency accuracies of a few per cent (plus or minus) are deemed acceptable. Circuit 78 includes gates 80 and 82, which may be either simple inverters, gates of other types "left over" in circuit packages and with inputs tied together or to appropriate logic levels so that they function as inverters, or, optionally, such gates with the additional inputs used to permit on-off control. For example, gate 80 is shown in FIG. 6 as a two-input NAND gate with one input 84a functioning in the oscillator and the other input 84b providing control, such that the oscillator runs only when this input is at a positive logic level. Similarly, gate 82 is also shown as a two-input NAND gate but with both inputs tied together so that the gate functions as a simple inverter.

The output 92 of gate 80 is connected to the inputs of gate 82, while resistors 86, 88 and a capacitor 90, respectively, connect input 84a, output 92, and output 94 of gate 82 to a circuit node 96 which is otherwise isolated.

Figure 7:
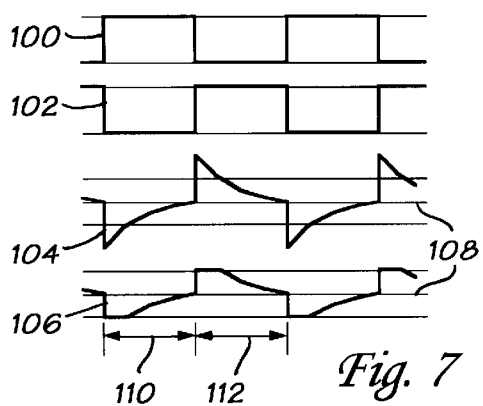
FIG. 7 illustrates the operation of the oscillator of FIG. 6.

The operation of oscillator circuit 68 is illustrated in FIG. 7. Lines 100, 102, 104 and 106 represent the voltages at output 92, output 94, node 96, and input 84a, respectively, as functions of time. Outputs 92 and 94 are complementary.

An upward transition of output 92 (shown as a voltage 100) causes an immediate downward transition in output 94 (shown as a voltage 102) which is relayed through capacitor 90 to node 96, causing a voltage 104 of node 96 to be lowered by a like amount. Since resistor 88 ties node 96 to output 92, which is now "high," voltage 104 then increases gradually, with a time constant determined chiefly by the product of resistor 88 and capacitor 90, toward the positive logic level.

A voltage 108, set approximately midway between the positive and negative supply levels (which for CMOS logic, approximately equal the logic output levels), represents the level of input 84a (a voltage 106) at which output 92 changes state. The exact value of voltage 108 depends on the specific type of device and manufacturing technology; however, the value of voltage 108 is reasonably consistent among devices of the same general type number (for example, CD4001B quad NAND gate ICs (integrated circuits)) from the same manufacturer.

Voltage 106 is approximately equal to voltage 104 as long as voltage 104 is between the positive and negative supply levels; however, voltage 106 is typically clipped above and below these levels by protective diodes within gate 90. Resistor 86 prevents this clipping action from drawing excessive current from node 96. Resistor 86 preferably has a value at least twice, and more preferably between five and ten times, the value of resistor 88.

The time needed for voltage 104 to decay from its initial value to a voltage 108 is shown in FIG. 7 as an interval 110. Provided that resistor 86 is sufficiently larger than resistor 88, interval 110 closely approximates the product of resistor 88 and capacitor 90 times the natural logarithm of 3, or approximately 1.10. By way of example, for values of 10,000 $\Omega$ for resistor 88 and 0.1 $\mu$f for capacitor 90, interval 110 is approximately 1.1 msec.

At the instant when voltage 106 first rises above voltage 108 (and provided that input 84b in FIG. 6, or equivalent inputs in other arrangements, is in the appropriate logic state to permit this action), gate 80 changes state and output 92 abruptly comes "low"; output 94 immediately goes "high," capacitor 90 relays the change to node 96, and voltages 104 and 106 are driven "high." The same voltage-decay process then takes place through resistor 88 as before, but in reverse since output 92 is now "low." Again, the time required is about 1.10 times the product of resistor 88 and capacitor 90. Hence, intervals 110 and 112 are equal (or approximately so) and the output is, at least to a close approximation, a square wave.

While the circuit of FIG. 6 is used in this way, it has not heretofore been recognized that intervals 110 and 112 can be made unequal, resulting in an output that is an approximately rectangular wave having essentially any desired duty cycle. Surprisingly, this result can be obtained simply by replacing resistor 88 with an asymmetrical resistive element or network.

A suitable resistive network may be formed by adding another resistor 120 in series with resistor 88 and shunting resistor 120 with a diode 122. In this arrangement, current flowing from node 96 toward output 92 "sees" only resistor 88 plus a slight voltage drop in the forward-biased diode, while current flowing from output 92 toward node 96 sees both resistors in series since diode 122 is now reverse-biased. Hence, in the corresponding voltage curves shown in FIG. 9, interval 110 is significantly longer than interval 112. Nearly any desired duty cycle can be attained simply by choosing the correct ratio between the two resistors 88 and 120. Similarly, reversing the direction of diode 122 makes interval 112 correspondingly longer than interval 110.

Additional network arrangements utilizing the above-described principle are also possible within the spirit of the present invention. As one of many possible examples, resistor 88 can be connected directly between node 96 and output 92 as shown in FIG. 6, but with the series combination of resistor 120 and diode 122 in parallel with resistor 88 so that one current polarity "sees" resistor 88 alone while the other "sees" resistors 88 and 120 in parallel.

Figure 2:
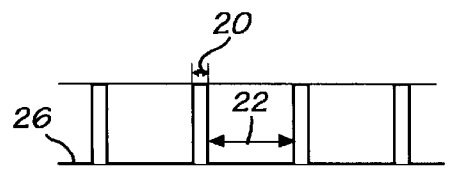
FIG. 2 shows a waveform used for the treatment of osteoporosis.
Figure 3:
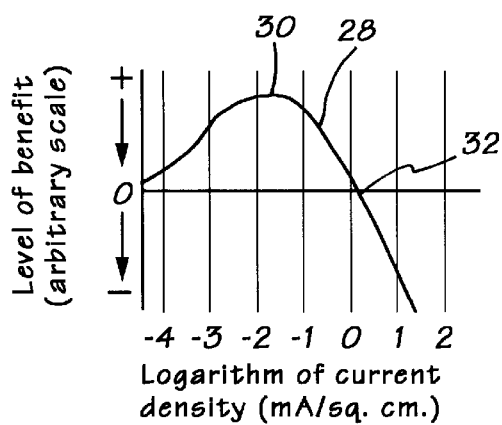
FIG. 3 is a graph showing the attained benefit versus the logarithm of applied current density.
Figure 4:
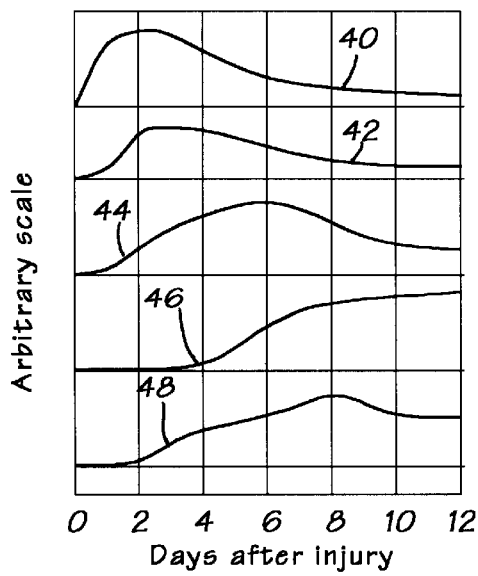
FIG. 4 illustrates the progression of healing in injured tissues.
Figure 5A:
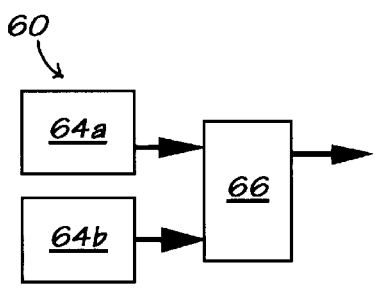
FIGS. 5A and 5B are schematic views of two prior art signal generators.
Figure 5B:
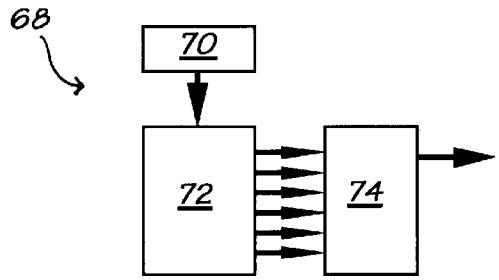

Such an asymmetric oscillator, by itself, can generate a continuous pulse train like that shown in FIG. 2. To generate an intermittent waveform of pulse bursts alternating with "quiet" periods, like the classic "Bassett-type" waveform shown in FIG. 1, requires a cascade or other logical interconnection between two such oscillators: either with the outputs of both combined by external logic (analogous to block diagram 60 in FIG. 5) or, preferably, with the lower-frequency oscillator running continuously but switching on the higher-frequency one only when it is needed. Such an arrangement is described below.

Figure 8:
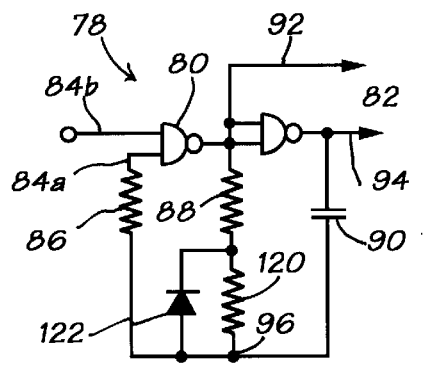
FIG. 8 is a circuit diagram of an oscillator circuit according to a preferred embodiment of the present invention.
Figure 10:
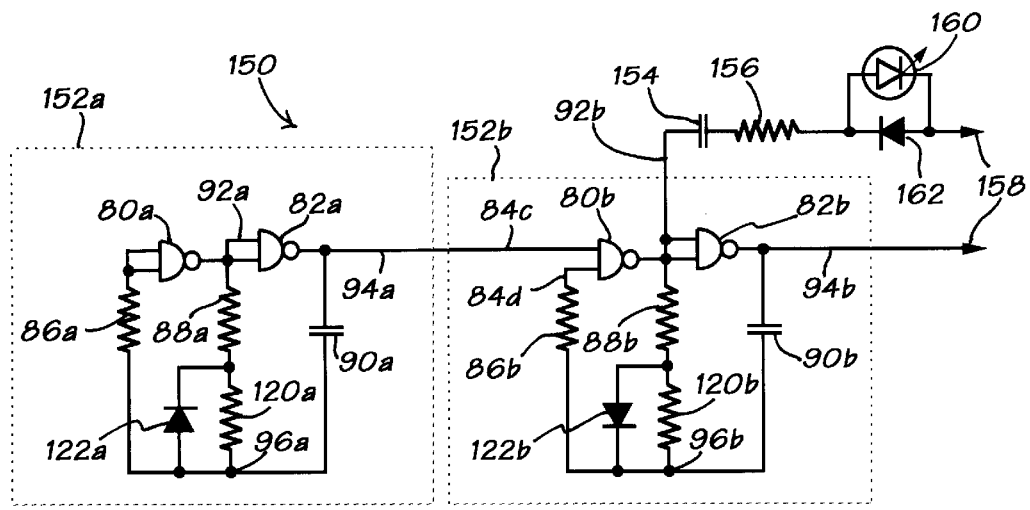
FIG. 10 is a circuit diagram of a signal generator according to a preferred embodiment of the present invention.

Referring now to FIG. 10, there is shown a signal generator 150 according to a preferred embodiment of the present invention. Generator 150 includes two oscillator sections 152a, 152b. For clarity, some of the components of generator 150 are given the same reference characters as appear in the circuit of FIG. 8; however, the suffix "a" or "b" is appended to differentiate components of the two oscillators 152a, 152b. An exception to this rule is made for the inputs to gates 80a and 80b, as will be explained further below.

Figure 9:
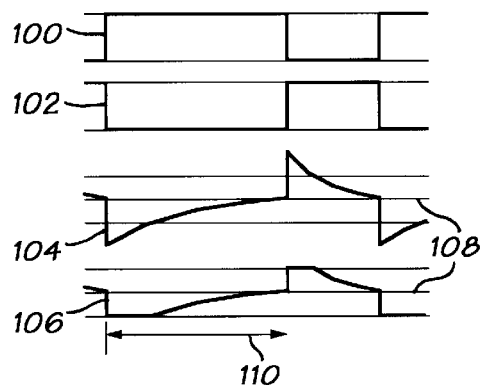
FIG. 9 illustrates the operation of the oscillator of FIG. 8.

Oscillator section 152a produces a waveform at output 94a consisting of alternating logic "low" and logic "high" periods corresponding respectively to intervals 110 and 102 in FIG. 9. Interval 110 further corresponds to interval 22 in FIG. 1 while interval 112 corresponds to interval 20. Output 94 is thus alternately "high" for about five msec, and "low" for about 62 msec. By way of example, an output 94 with these properties may be achieved by selecting a capacitor 90a of about 0.1 $\mu$f, a resistor 88a of about 43,000 $\Omega$, a resistor 120a of about 510,000 $\Omega$ and a resistor 86a of any convenient value from about 2.2 M $\Omega$ up. Of course, other values for these components may also be useful for the practice of the invention. Because of normal type-to-type and manufacturer-to-manufacturer variations in gate threshold voltage 108, the optimum values of these components are determined by a modest amount of experimentation and observation for each particular application and type of component.

In oscillator 152a, gate 80a acts as a simple inverter with its input(s) driven solely by the voltage relayed through resistor 86a from node 96a. Output 92a from this gate is used only to drive the input(s) of gate 82a and the network of resistors 88a and 120a and diode 122a, and does not leave block 152a.

Output 94a, with the characteristics already described, leaves block 152a and passes into block 152b, where it is applied to input 84c of gate 80b to provide on-off switching of gate 80b. When input 84c is low, output 92b is always "high," output 94b is always "low," and no oscillation takes place. Node 96b rapidly takes on the same voltage as output 92b; once this occurs, the current drawn by the oscillator block is in the range of a few nanoamperes. When input 84c is "high," however, gate 80 acts as an inverter driven by input 84d and block 152b oscillates in the manner previously described, producing complementary signals on outputs 92b and 94b.

Since the desired output during interval 20 (as measured at output 92b) consists of a series of positive pulses which are relatively longer than the intervals between them, while the desired output during interval 22 is negative, diode 122b preferably has an orientation opposite that of diode 122a. This permits oscillator block 152b to generate a negative interval 18 which is shorter, by any desired ratio, than positive interval 16. For the preferred "Bassett-type" pulse intervals of 28 $\mu$sec and 200 $\mu$sec, respectively, capacitor 90b may have a value of approximately 0.001 $\mu$f, resistors 88b and 120b values of about 22,000 and 150,000 $\Omega$ each, and resistor 86b any convenient value from about 680,000 $\Omega$ up. For example, resistors 86a and 86b may have equal values e.g. of 2.2 M $\Omega$ each. Because of normal type-to-type and manufacturer-to-manufacturer variations in gate threshold voltage, the optimum values of these components are determined by a modest amount of experimentation and observation for each particular application and type of component.

Outputs 92b and 94b are complementary, so the AC components of the voltage measured between them will be twice those of either output alone. Capacitor 154 blocks all DC components of the signal, and resistor 156 helps to minimize the effects of skin resistance, so that the final output signal which appears between output terminals 158 is appropriately current-limited, contains no net DC, and consists either of the classic "Bassett" waveform or of another waveform selected for the particular application in view. If a visual indication of output is desired, a light-emitting diode 160 or other suitable device may be placed in series with the output as well. Since LED 160 blocks the reverse flow of current, a signal diode 162 is preferably set antiparallel to LED 160 to furnish a path for this current. It may be noted here that capacitor 154, resistor 156, and the antiparallel combination of diodes 160 and 162 (if used) may be placed indifferently in series with either output 92b, 94b, or distributed in any fashion between these lines, as may be most convenient.

Alternatively, resistor 156 may be replaced with a potentiometer (not shown) so that the user can regulate the amplitude of the output current. This ability is particularly useful for applications such as TENS, where the signal amplitude is preferably set as high as possible without its being directly perceptible to the user. For muscle stimulation, an even higher setting may be desirable, since an electrically-induced muscle twitch will almost certainly be noticed by the user but too-strong twitches are perceived as being annoying. Furthermore, individual thresholds for sensation, discomfort, and outright pain vary widely. Therefore, a device with a potentiometer, or other adjustable amplitude-controlling means, allows the user to set a stimulation level which strikes a balance between comfort and effectiveness.

Yet another modification to the output side of circuit 150 is accomplished by replacing resistor 156 with the primary winding of a small audio transformer (not shown) of the sort commonly found in transistor radios. This permits the output voltage to be stepped either up or down, as might best suit the specific requirements of the application.

Figure 11:
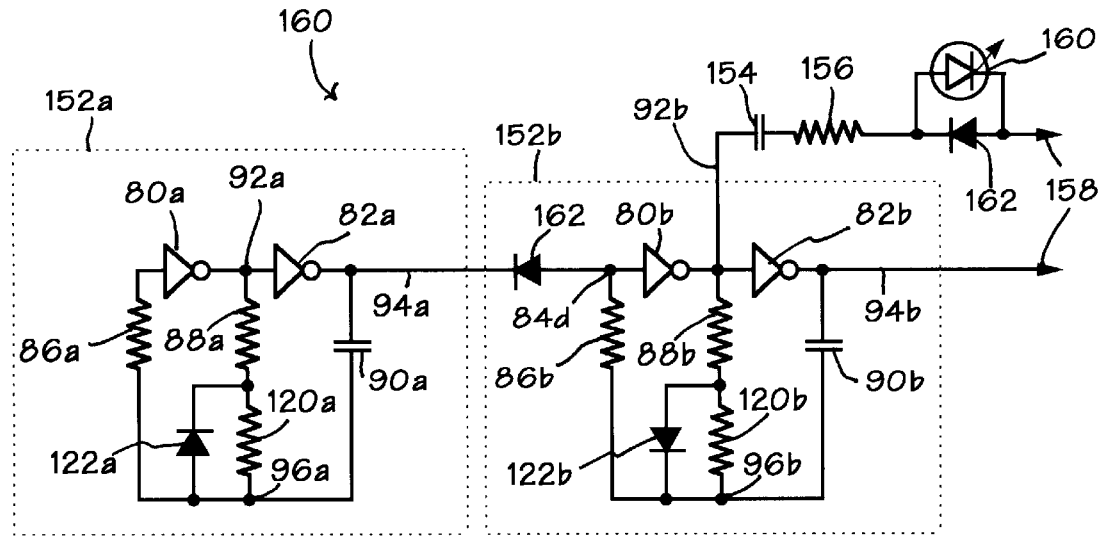

Another embodiment 160 of the present invention, shown in FIG. 11, differs from the embodiment of FIG. 10 chiefly in that logic gates 80a, 82a, 80b and 82b are simple inverters. This permits the use of relatively high-current-capacity logic buffers or data-line drivers such as those in the CD4049UB or CD4069UB hex inverter packages. Switching of high-frequency oscillator block 152b is accomplished by placing a single additional diode 162 between output 94a and input 84d. With output 94a "low," input 84d is held at logic "low" regardless of the voltage at node 96b. Because output 92b is "high," some small current flows through the series combination of resistors 86b, 88b and 120b and thus it is advantageous to make resistor 86b, at least, as large as possible.

Further power reduction can be achieved by giving capacitors 90a and 90b values as small as practical. In general, however, values less than approximately 100 pf are less useful since the gates' effective input capacitances may vary by a significant fraction of this amount due to nonlinear space-charge effects in the semiconductor material. In addition, resistance values are preferably less than approximately 10 M Ω due to the possibility of interference by current leakage in the reverse direction through diode 162 for higher resistances, or, especially in humid weather, over the surfaces of the various circuit components.

Practical ranges of values for the resistors and capacitors in circuit 160 are the same as for circuit 150, therefore, save that, if practical, the resistance of resistor 86b should be in the range between approximately 2.2 M Ω and 10 M Ω, inclusive.

Figure 12:
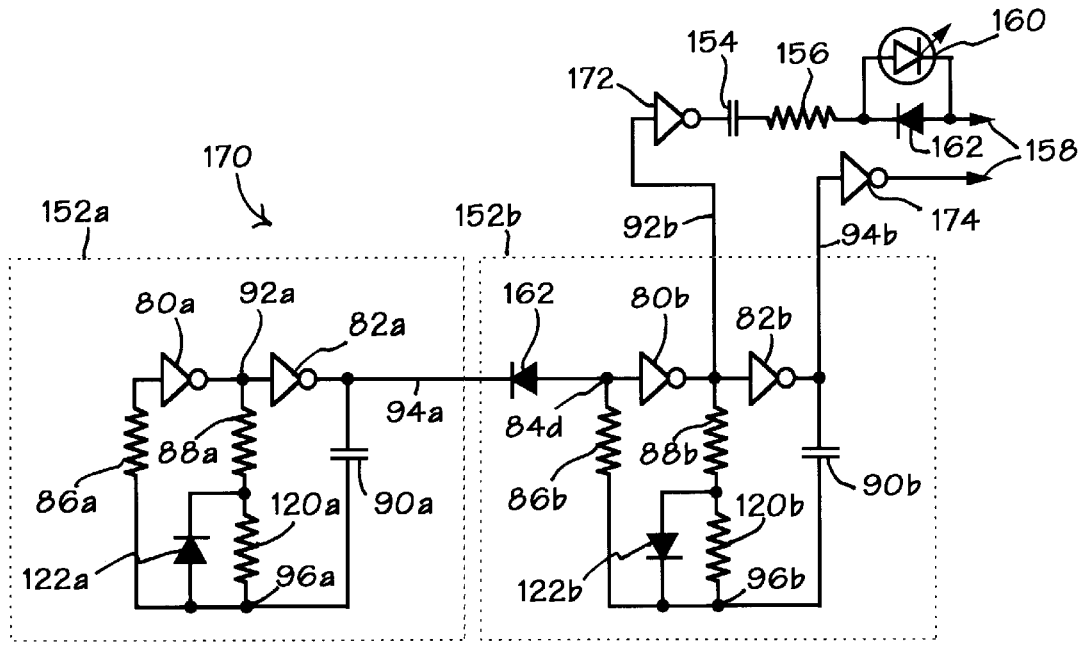

An advantage of using integrated-circuit packages such as the CD4049UB or CD4069UB is that, since there are six inverters in such a package, two of the inverters may be used to buffer the outputs and thus isolate the internal, timekeeping portions of the circuit from possible interference from outside electrical noise or changes in loading. This is shown in the circuit of FIG. 12, where gates 172 and 174 serve as the output buffers and are driven by outputs 92b and 94b, respectively. As before, capacitor 154 and resistor 156 are placed in either output line—in this case, either that following buffer 172 or that following buffer 174—to remove the DC component from the output signal and lessen the effect of skin resistance. LED 160 and diode 162 may also be added if a visual confirmation of output is desired. Also as before, the arrangement and distribution of these components between two output lines, leading to output terminals 158, is of no practical consequence.

In any of the specific embodiments described above, terminals 158 are preferably designed to accept flexible cables leading to electrodes (not shown) which make contact with the tissues to be treated, or to adjacent skin areas. These may be TENS-type, self-adhesive skin electrodes, although other electrode types may be useful for some applications.

To illustrate the versatility of the present invention, FIG. 13 shows an alternative preferred embodiment in the form of a block 270 wherein resistor 156 is placed in one output line, diodes 160 and 162 in the other output line and with opposite polarity to that shown in FIG. 12, and capacitor 154 is replaced by two electrolytic capacitors 154a and 154b, one set in each line but both with their anodes facing the output buffers, thereby blocking DC coming from either direction. Either of lines 92a, 92b from block 152b can feed either oscillator, or, as in FIG. 11, the buffers may be omitted. Alternatively, capacitors 154a, 154b may be set one in each output line as shown but with their cathodes facing the buffers; both capacitors may be set in the same output line with either their two anodes or their two cathodes connected together; or nonpolarized capacitors, for example large monolithic ceramic types, may be substituted in either or both lines.

Still another embodiment of the invention provides a swept frequency signal by incorporating frequency scanning with basic oscillator circuit 78 of FIG. 6. The resulting voltage-controlled oscillator (VCO) 200 is shown in FIG. 14A. For simplicity, the logic gates are shown here as simple inverters, although many other gate types may be used. Voltage control of the output frequency of VCO 200 is achieved by varying the effective threshold voltage $V_e$, that is, the voltage at node 96 at which gates 80 and 82 change their output logic states. This may be done by applying a control voltage $V_c$ through a resistor 202 connected to the input of inverter 80. The resulting threshold voltage $V_e$ is that at which the voltage-dividing action of resistors 204 and 86 places the input of gate 80 at its true threshold voltage $V_{th}$, which for standard CMOS logic circuits is typically close to one-half the supply voltage $V_s$.

Oscillator 200 has the roughly parabolic voltage-to-frequency characteristic shown in FIG. 14B. The generated frequency f is at a maximum when $V_c$ equals $V_{th}$, and decreases, at first slowly and then more rapidly, with a change in either direction. The response of oscillator 200 may be made monotonic by adding another resistor 204 connecting the input of gate 80 to either the positive or the negative (ground) supply rail. Resistors 202 and 204 each have values greater than that of resistor 86, which in turn is at least twice and preferably several times the resistance of timing resistor 88.

When resistors 202 and 204 are equal, and resistor 204 is connected to the positive supply as shown in FIG. 14A, the frequency is at its maximum when the control voltage is at ground and decreases to a minimum as this voltage is raised, as shown in FIG. 14C. When resistor 204 is grounded instead, the frequency will increase with the control voltage as shown in FIG. 14D. In effect, either of these approaches selects just one-half of the parabola of FIG. 14B. A more nearly linear frequency response (as shown in FIG. 14E) may be obtained by making resistor 204 lower in value than resistor 202, although at the expense of some of the frequency variability.

The relationships among $V_c$, $V_e$, $V_s$, $V_{th}$, the positive output period $t_1$, the negative output period $t_2$, and the output frequency f are given by the following equations:

$$V_e = V_{th}(R_f/R_b + R_f/R_i + 1) - V_s(R_f/R_b) - V_c(R_f/R_i),$$

$$t_1 = R_t C_t \ln((V_s + V_e)/V_e),$$

$$t_2 = R_t C_t \ln((2V_s - V_e)/(V_s - V_e)), \text{ and}$$

$$f = 1/(t_1 + t_2),$$

where $R_t$ is the value of timing resistor 88, $C_t$ that of timing capacitor 90, $R_f$ that of feedback resistor 86, $R_i$ that of input resistor 202, and $R_b$ that of biasing resistor 204. In general, $R_i \approx R_b$ and $R_b > R_f > R_t$. $V_c$, $V_e$, $V_s$ and $V_{th}$ are given in volts, $t_1$ and $t_2$ in seconds, f in Hertz (cycles per second), all resistances in M Ω, and $C_t$ in µf (microfarads). For standard CMOS gates and where $R_i = R_b$:

$$V_e \approx 0.5V_s - V_c(R_f/R_i)$$

For example, assuming ideal components with $R_i$ and $R_b$ each equal to 10 M Ω, $R_f$=2.2 M Ω, $R_t$=1 M Ω and $C_t$=0.001 µf, the output frequency of VCO 200 is about 455 Hz at $V_c$=0 volt, about 446 Hz at $V_c$=0.5 $V_s$, and about 418 Hz at $V_c$=$V_s$. As shown in FIG. 14C, the output frequency changes only slowly as $V_c$ first leaves the neighborhood of ground, then more and more quickly as $V_c$ nears $V_s$. For any given value of $V_c$, the output frequency is approximated by:

$$f = 455 + 1.1(V_c/V_s) - 37.7(V_c/V_s)^2.$$

The change in frequency is due to the interplay between an increase in $t_1$ and a smaller decrease in $t_2$ as $V_c$ is raised. For the component values given above and with $V_c$=0 volt, $t_1$ and $t_2$ are each 1100 microseconds; with $V_c$=0.5$V_s$ they are 1270 and 970 microseconds, respectively, and with $V_c$=$V_s$, 1520 and 870 microseconds, respectively. Hence, the waveform becomes more asymmetric as $V_e$ departs from $V_{th}$ and the frequency decreases.

The nonlinearity in the relationship of the output frequency to the control voltage can be corrected in any of several ways, including by piecewise synthesis of a new control voltage as a function of the old one. For example, a scan of frequency across the usable range at a rate nearly constant with time can be achieved by applying a control voltage which changes quickly in those ranges where the frequency response of oscillator 200 to voltage is weak, and more slowly in regions where it is strong.

Since most biological systems tend to show a logarithmic, rather than linear, response to outside stimuli, strict linearity is less important for biomedical than for many instrumental applications. For example, the human ear interprets successive musical notes on a piano keyboard as being equally spaced in frequency even though the actual frequency spacing is logarithmic: each octave has a frequency ratio of two, and each pair of adjacent keys (including sharps and flats) a ratio of about 1.0595 (the twelfth root of two). Similarly, the brightness of stars as they appear to the eye forms a logarithmic scale: stars which appear to be one magnitude apart actually differ in brightness by a ratio of about 2.5. While not wishing to be bound by theory, it is believed that the bioeffectiveness of electrical signals follows an analogous trend. Therefore, for maximum effectiveness, a frequency-scanning bioelectronic stimulator would pass through its frequency range of operation in a logarithmic, rather than a linear, fashion when the frequency is plotted as a function of time.

Above-described VCO 200 may be given a more asymmetric output waveform by replacing resistor 88 with an asymmetric resistive element or network. For example, a signal generator circuit 218 (shown in FIG. 15A) takes a different form from that shown in FIGS. 8 and 10–12: a VCO 220 is here formed by two resistors 210a and 210b placed in parallel (rather than in series as before) and with a diode 212 in series with the lower-valued member 210a of the pair. Current passing in the reverse diode direction thus "sees" the full resistance of resistor 210b, while current passing in the diode's forward direction sees the parallel combination of both resistors plus a small contribution from the diode's forward voltage drop. Neglecting the forward drop, the output timing characteristics are then given by:

$t_1 = R_r C_r \ln((V_s + V_e)/V_e)$, $t_2 = R_p C_r \ln((2V_s - V_e)/(V_s - V_e))$, and $f = 1/(t_1 + t_2)$, where $R_r$ is the value of resistor 200a alone, $R_p$ is that of resistors 210a and 210b in parallel, and diode 212 has the orientation shown in FIG. 15A. When this is so, and because $R_p$ is necessarily smaller than $R_r$, $t_1$ is invariably longer than $t_2$. With diode 212 reversed, as is diode 232 in oscillator 222 (to be described below), $R_r$ and $R_p$ trade places in the above equations, making $t_2$ longer than $t_1$. In either case, resistor 86 and capacitor 90 function as before.

Thus, the circuit of FIG. 15A is a surprisingly simple signal generator wherein asymmetric VCO 220 can be both switched on and off, and frequency-modulated (when on) by another oscillator 222, producing a very nearly logarithmic change of frequency as a function of time despite its own inherent nonlinearity. Control oscillator 222 is nearly identical with VCO 220, being formed by gates 224a and 224b (shown in FIG. 15A as simple inverters), a resistor 226, a capacitor 228, and an asymmetric resistive element formed by resistors 230a, 230b and a diode 232, here again connected with the resistors in parallel as in FIG. 14A. Connecting the two VCOs 220 and 222 together, along with resistor 202, are a switching diode 240, a control resistor 242 and a control capacitor 244.

When the output of control VCO 222 is low, diode 240 is forward-biased and the input of gate 80 is held well below $V_{th}$, so that VCO 220 cannot oscillate at all. In this situation, an output 248a is held constantly at logic high (close to $V_s$) and an output 248b at logic low (close to ground). Capacitor 244 also discharges to near ground potential through resistor 242.

When the output of VCO 222 becomes high, diode 240 becomes reverse-biased and turns off. VCO 220 is thereby enabled and begins to oscillate at a frequency which is controlled by the voltage applied through resistor 202, producing complementary outputs at 248a and 248b in the manner explained previously. The voltage on capacitor 244, however, is constantly rising as capacitor 244 charges through resistor 242. If the values of resistors 86, 202 and 204 are chosen so as to have the correct ratios, the nonlinearity of the charging rate will partly cancel that of the voltage-to-frequency conversion, resulting in an output frequency which, surprisingly, is approximately logarithmic with time over as many as three charging time constants of capacitor 244.

Figure 15B:
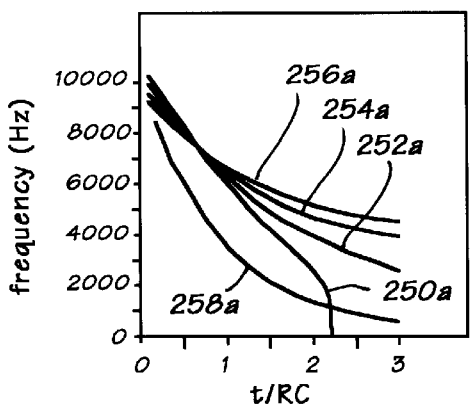
FIGS. 15B and 15C illustrate the operation of the generator of FIG. 15A.

FIG. 15B shows the calculated frequency output of the circuit of FIG. 15A as a function of time for four different values of resistor 202 (curve 250a, 2.2 M Ω; curve 252a, 2.7 M Ω; curve 254a, 3.3 M Ω; curve 256a, 3.9 M Ω). The values of resistors 86, 204, 210a and 210b are held constant at 2.2 M Ω, 10 M Ω, 10,000 Ω and 100,000 Ω, respectively; capacitor 90 has a constant value of 0.001 μf, and all other circuit components are assumed to have ideal (or approximately so) characteristics. Curves 250a through 256a approximate logarithmic decay curves, but with time constants considerably longer than the charging time constant of capacitor 244 (as indicated by the bottom scale on FIG. 15A). For comparison, curve 258a represents a frequency which decays with the same time constant with which capacitor 244 charges. The difference is due chiefly to the nonlinear response of VCO 220.

The differences between these curves are more clearly seen when the proportional rate of decay—that is, df/(fdt) where f is the frequency and t is time—is plotted as a function of time. Where f decays logarithmically—that is, $f = ke^{-at}$ where k and a are constants—then $df/dt = -ake^{-at}$ and $df/(fdt) = -ake^{-at}/ke^{-at} = -a$, a simple constant. Hence, a plot of df/(fdt) is a straight horizontal line if the decay is truly logarithmic, close to horizontal if the decay is approximately logarithmic, but not otherwise.

Figure 15C:
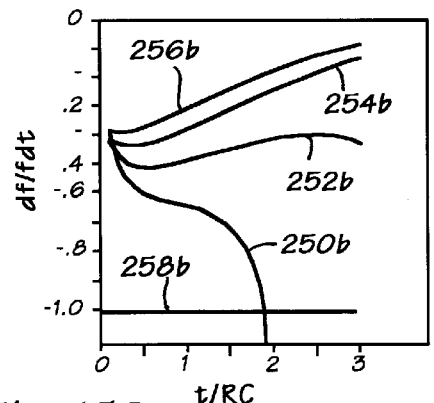
Figure 16:
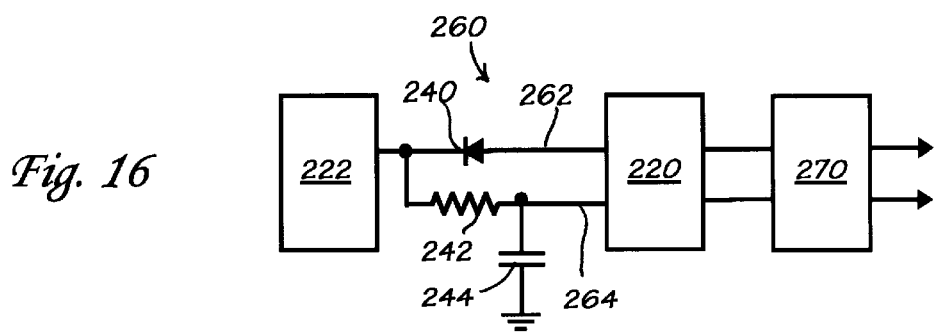
FIGS. 16, 17A–C, 18, 19A, 19B, 20A–C are additional signal generators according to the invention.

FIG. 15C shows plots 250b, 252b, 254b and 256b of df/(fdt) as functions of time, each corresponding to the like-numbered curve in FIG. 15B. Time is shown in unit increments of RC, the time constant with which capacitor 244 charges. Similarly, curve 258b represents df/(fdt) for a frequency which decays with a time constant equal to RC. As can be seen, curve 258b is flat with a constant value of −1. While curves 250b, 252b, 254b and 256b are not flat, curve 252b, representing a value of 2.7 M Ω for resistor 202, is nearly so over the range of interest, showing that for these resistor ratios ($R_f = 4.5 R_b$ and $R_t = 1.2 R_b$), the frequency change closely approximates the desired logarithmic rate. Since these ratios were calculated assuming ideal CMOS gates, however, it may be found that specific real-world components may require slightly different ratios to be determined in each case through a modest amount of experimentation.

While curve 252b is approximately flat, the curve lies within a negative range of only about −0.4 to −0.5, showing that the effective time constant of the exponential decay is a little more than twice RC. Hence, as compared with a linear VCO which might be used for the same purpose, and for a frequency scan at the same rate, this circuit would require a capacitor with a value only about 40% to 50% as large, and thus be potentially both cheaper and better-suited to miniaturization.

Alternatively, a commercially-available integrated device such as the TLC555 CMOS timer, TLC556 dual CMOS timer, NE566 voltage-controlled oscillator, or other suitable device, along with various passive components, could be substituted either for VCO 220, control oscillator 222, or both, without drastically changing the performance of signal generator 218, save for the output frequency decay pattern and the frequency range over which it occurs. FIGS. 17–20 are examples of such substitutions.

For purposes of simplification in describing the embodiments of FIGS. 17–20, FIG. 16 shows a signal generator 260 where VCO 220 and control oscillator 222 of FIG. 15A are shown as blocks connected by a forking signal line, wherein an upper branch 262 of the fork represents the on/off control input to VCO 220 and a lower branch 264 represents the control voltage input via resistor 202. Similarly, a block 270 represents an output network, for example, a network such as the one shown in FIG. 13. Apart from these changes, all components shown in FIGS. 17–20 which appeared in the preceding Figures are given the same reference characters as before.

Figure 17A:
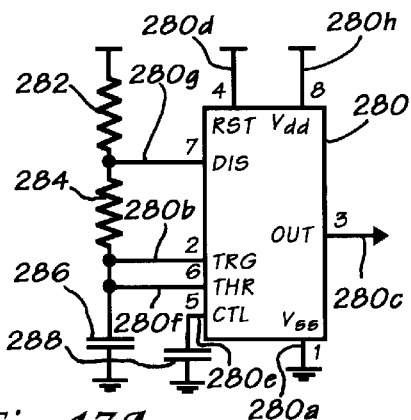

Another preferred embodiment of the present invention, partially shown in FIG. 17A, uses a control oscillator 222 (as described above) driving an alternative type of voltage controlled oscillator built around a commercial TLC555 integrated-circuit timer or equivalent CMOS device 280 with suitably low operating current. Here, device 280 has pins 280a, 280b, 280c, 280d, 280e, 280f, 280g, 280h, representing standard pins 1–8, respectively, of device 280. Device 280 is powered by connecting the positive supply voltage $V_s$ to pin 280h and pin 280a to ground. Pin 280d (pin 4, "reset") must be pulled close to $V_s$ for the selected CMOS device to operate. Pin 280c provides the output, which at any given instant is either high (close to $V_s$) or low (close to ground). Astable oscillation is achieved by connecting a resistor 282 between the positive supply and pin 280g, a second resistor 284 between this and pins 280b and 280f (tied together), and a capacitor 286 between these pins and ground. Pin 280e may either be left disconnected or bypassed to ground through a capacitor 288. Thus connected, device 280 oscillates with a high period $t_1$, low period $t_2$, and frequency $f_0$ which are determined by $R_a$, $R_b$ and $C_t$ where these are the values of resistor 282, resistor 284 and capacitor 286 respectively:

$$t_1=(R_a+R_b)C_t\ln 2$$

$$t_2=R_b C_t \ln 2$$

$$f_0=1/(t_1+t_2)$$

Pin 280e normally floats at a voltage $V_p$ which is about two-thirds of the supply voltage $V_s$, as set by a resistive voltage divider within device 280. If the voltage $V_c$ of pin 280e is pulled away from $V_p$ by outside circuitry, however, the oscillation timing will also change, and thus device 280 may be used as a VCO:

$$t_1=(R_a+R_b)\,C_t\ln((V_s-0.5V_C)/(V_S-V_C))$$

$$t_2=R_b C_t \ln 2$$

$$f=1/(t_1+t_2).$$

Figure 17B:
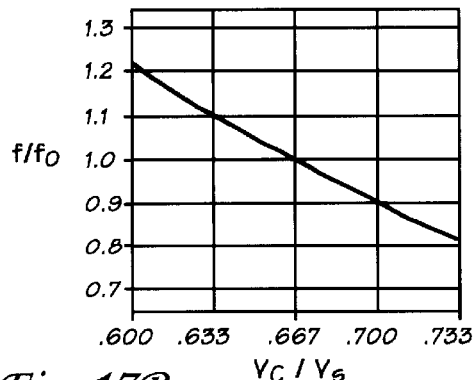

A portion of the resulting voltage-to-frequency response is shown in FIG. 17B. The frequency f decreases as $V_C$ increases, with a characteristic curve which is approximately linear in the range close to $V_p$.

Figure 17C:
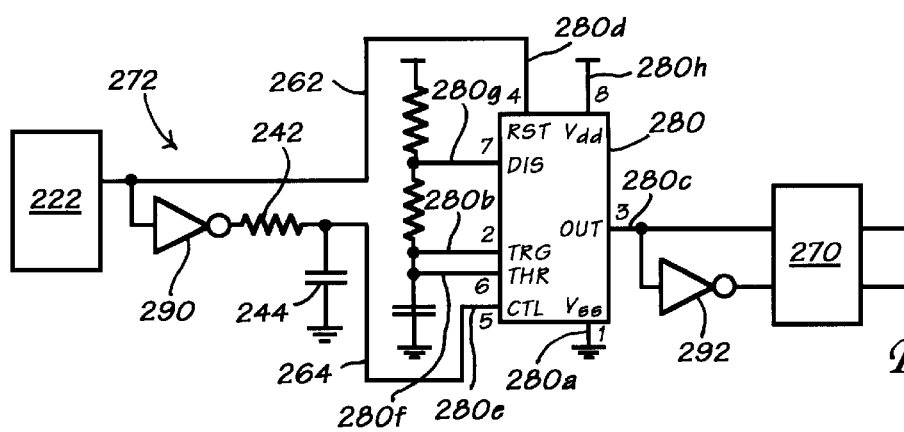

An integrated circuit device such as device 280 may be driven by the previously-described control oscillator 222, generating an approximately logarithmic frequency output, by connecting the two devices together as shown in FIG. 17C. Here, a signal generator 272 has a line 262 driving pin 280d; device 280 is "reset," or held in a nonoscillating state, when pin 280d is "low," but permitted to oscillate when the pin is "high." Line 264 is driven through an inverter 290, so that the line is "low" when line 260 is "high," and vice versa. Since device 280 as shown does not provide complementary outputs, another inverter 292 is preferably added at output pin 280c to generate the second, complementary signal needed to drive block 270.

Resistor 242 and capacitor 244 have the functions described above, save that provision is made for the relatively low impedance of pin 280e resulting from the presence of the internal voltage divider: only about 60,000 ohms in a TLC555 as compared with the several megohms of resistor 202 in the above-described embodiments of the invention. Hence, resistor 242 must be considerably lower and capacitor 244 proportionally larger, or a voltage buffer such as an operational amplifier connected for unity gain is added between capacitor 244 and pin 280e (in either case, the supply current requirements are increased significantly above those of the third embodiment). Any specific adjustments depend on the particular selection of integrated circuit device 280.

Figure 18:
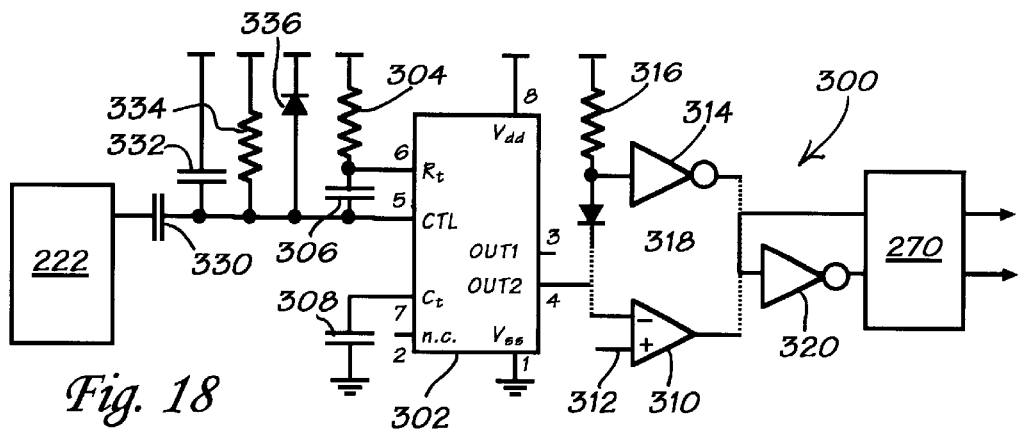

Another signal generator 300 according to the present invention is shown in FIG. 18, wherein an LM566, NE566, or similar commercially-available voltage-controlled oscillator device 302 replaces above-described device 280, connected generally as shown. Pin 5 acts as the control input, and unlike pin 5 of above-described device 280, has a high impedance typically around one megohm. A resistor 304 and a capacitor 308 are the timing components, represented in the following equation by $R_t$ and $C_t$, respectively. A capacitor 306 is used as a bypass device to add stability to signal generator 300; its value is not critical, but is typically in the range of 0.001 μf. $R_t$ is approximately 2000–20,000 Ω. With a voltage $V_c$ applied to pin 5, this voltage being in the upper quarter of the supply-voltage range (that is, approximately 75–100% of $V_s$), the output frequency is given by:

$$f=2(V_s-V_c)/(R_t C_t V_s)$$

Since the main output of device 302 takes the form of a square wave at pin 3, with a duty cycle $t_1=t_2=1/(2f)$, additional circuitry may be needed in order to convert the output to a more asymmetric form. For example, since pin 4 provides an auxiliary, triangle-wave output swinging from about 30% to about 50% of the supply voltage, a voltage comparator 310 with an appropriate reference level 312 can be used to create an output having almost any desired duty cycle. Alternatively, a CMOS gate or simple inverter 314 could be connected to pin 4 with a slight DC voltage shift, for example by means of a resistor 316 and a diode 318, so that the shifted output waveform crosses its input transition voltage for the desired fraction of each cycle and causes its output to shift logic states, thereby creating the desired output. Both implementations are shown in the FIG. 18; the dashed lines indicate that either voltage comparator 310 or inverter 312 may be connected between pin 3 and the output as indicated. In either case, an extra gate or inverter 320 can be used to create an output complementary to the first.

Device 302 is driven by oscillator 222, which is generally similar to oscillator 222 as shown in FIG. 15A except that either diode 232 is reversed, or the output is taken from gate 224a rather than gate 224b, to make the positive output period $t_1$ longer than the negative period $t_2$. This signal is applied to an AC voltage divider formed by capacitors 330 and 332, capacitor 332 having preferably about three times the value of capacitor 330. $V_c$ is taken from the node joining capacitors 330, 332 and applied to pin 5 of device 302. The 3:1 ratio of capacitors 330, 332 ensures that $V_c$ is approximately 0.75Vs immediately after a downward transition of the output of oscillator 222. $V_c$ then decays toward $V_s$ through a resistor 334. Since the voltage-to-frequency characteristic of device 302 is approximately linear, the decay time constant of the output frequency is the same as that of $V_c$, or the product of the value of resistor 334 (in parallel with the high input impedance of pin 5) multiplied by the sum of the values of capacitors 330 and 332. Upon an upward transition, the voltage at pin 5 is clamped by a diode 336 to one forward voltage drop (about 0.7 volt) above the positive supply, thereby preventing damage to device 302.

Despite a somewhat higher battery drain (due to the relatively high operating current of device 302) than the embodiment shown in FIG. 15A, the embodiments of FIGS. 17C and 18 generate an approximately logarithmic scan across a wider range of output frequencies.

Figure 19A:
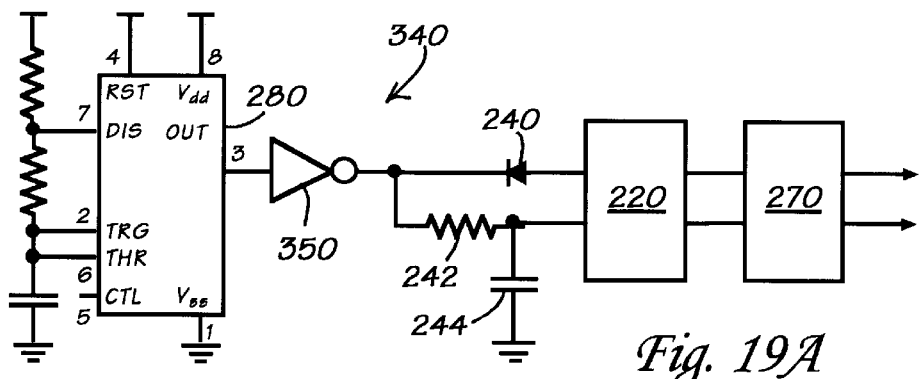
Figure 19B:
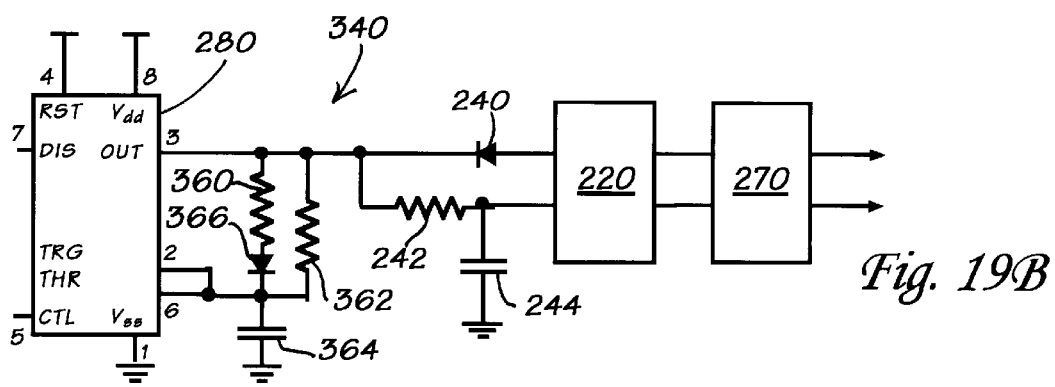

Still another embodiment of the invention is shown in FIGS. 19A and 19B, wherein a TLC555-type device 280 is connected as the control oscillator driving VCO 220 in a signal generator 340. Device 280 may be connected in astable mode wherein the output from pin 280c (i.e., pin 3) is inverted by a buffer 350 before feeding VCO 220 (FIG. 19A). Output high period $t_1$ of pin 280c is always greater than low period $t_2$, since $t_1=(R_a+R_b)C_t\ln2$, $t_2=R_bC_t\ln2$ and $R_a+R_b$ is greater than $R_b$ alone. Thus, to obtain the relatively short $t_1$ needed to drive VCO 220, the output from a device 280 connected in standard astable mode must be inverted. Then, diode 240, resistor 242, capacitor 244, VCO 220 and output block 270 can function as described above.

In FIG. 19B, device 280 is connected in an alternative mode, using a single feedback resistor or an asymmetric resistive network (as shown above in FIGS. 8 and 15) so that signals with any desired periods $t_1$ and $t_2$ can be generated according to the following relationships (neglecting diode voltage drops):

$t_1=R_pC_t\ln2$, $t_2=R_tC_t\ln2$, and $f_0=1/(t_1+t_2)$, where $R_1$ is the value of resistor 362 alone, $R_p$ that of resistors 360 and 362 in parallel, and $C_t$ that of capacitor 364. This yields the relatively short $t_1$ and long $t_2$ which are desired. Under these conditions, diode 240, resistor 242, capacitor 244, VCO 220 and output block 270 function as described above.

Yet another embodiment of the present invention takes advantage of the fact that the TLC555 integrated CMOS timing circuit is also offered in a dual version, the TLC556. Accordingly, one of the two TLC555 devices included in the package can replace control oscillator 222 and the other VCO 220, as in a signal generator 370 shown in FIG. 20A; the output circuit, with the two devices indicated as 372, 374, is identical with that of FIG. 17C. Except as described below, the operation of each of the two TLC555s 372, 374 is nearly identical with that of the corresponding device shown in FIGS. 17C or 19B.

In integrated circuit devices such as the TLC555, pin 7 (i.e. above-described pin 280g) is normally used for timing and pin 3 (i.e., pin 280c) is normally used for output to other circuitry. However, both pins 280c and 280g actually function as outputs, operating in synchrony but not internally connected. Pins 280c and 280g differ in that, while pin 280c can either sink or source current in the manner of a CMOS gate, pin 280g can only sink current and, when "high," appears as an open circuit. This feature of TLC555-type devices makes it possible to interconnect the two devices in a TLC556 package for use in a frequency-scanning pulse generator according to the invention. In this type of device, the control oscillator (device 372) is configured as shown in FIG. 19B, setting $t_1$ less than $t_2$, and its pin 3 (i.e., pin 280c) output is connected to pin 4 (i.e., pin 280d) of the VCO (device 374). Pin 7 (i.e., pin 280g) of the control oscillator is connected to pin 5 (pin 280e) of VCO 374 and bypassed to ground by a capacitor 380. No other interconnections are needed.

During low period $t_2$ of control oscillator 372, both of its outputs (pins 3 and 7) are low and its pin 3 pulls pin 4 of VCO 374 low in turn. VCO 374 is thus disabled, with its own outputs held low also. Hence, no VCO oscillation takes place during period $t_2$. At the same time, pin 7 of the control oscillator 372 pulls pin 5 of VCO 374 low, and discharges capacitor 380 to ground.

At the beginning of high period $t_1$, pin 3 of control oscillator 372 goes high, pulling pin 4 of VCO 374 high also and enabling oscillation. At the same time, pin 7 turns off, becoming an open circuit. Capacitor 380 is then recharged slowly by the internal voltage divider, and at a logarithmically decreasing rate, back toward $(2/3)V_s$. The time constant for this recharging is the value of capacitor 380 multiplied by the impedance of pin 5, which is typically about 60,000 Ω. The resulting changing control voltage $V_c$ causes VCO 374 to generate a changing output frequency f. A curve 390 (FIG. 20B) shows $V_c$ as a fraction of $V_s$ over three recharging time constants, while a curve 392a shows the resulting frequency f where resistor 282, resistor 284 and capacitor 286 have values of 100,000 Ω, 10,000 Ω, and 0.01 μf, respectively.

While curve 392a decreases asymptotically toward an approximately constant final value, corresponding to f at $V_c=(2/3)V_s$, the decrease is extraordinarily rapid at first and the final value is nonzero (in fact, it is 1202 Hz). Thus, the frequency decay is not logarithmic. In contrast, curve 394a shows a truly logarithmic decay starting from the same initial value as curve 392a. The difference is seen still more dramatically in FIG. 20C, comparing curves 392b and 394b: curve 392b shows df/(fdt), while curve 394b represents true logarithmic decay with df/(fdt) equal to a constant (−1).

EXAMPLE 2

Figure 20A:
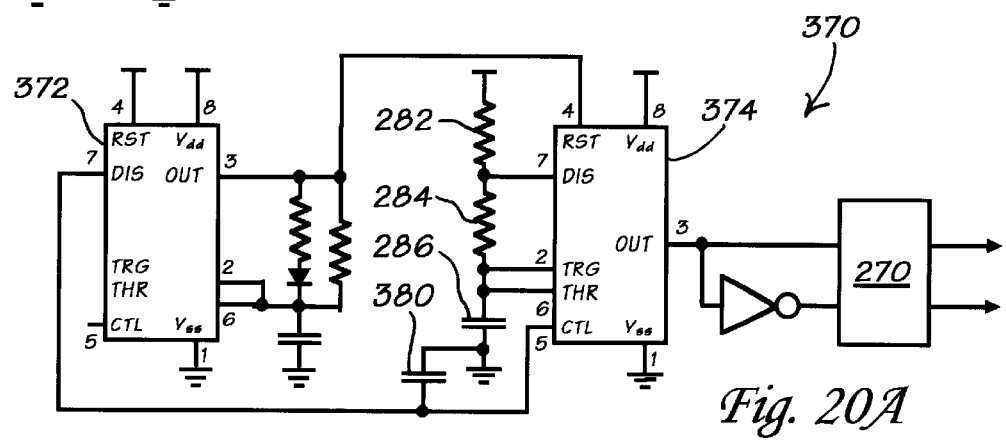
Figure 20B:
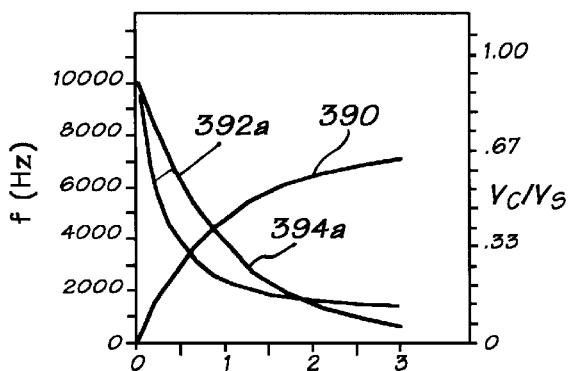
Figure 20C:
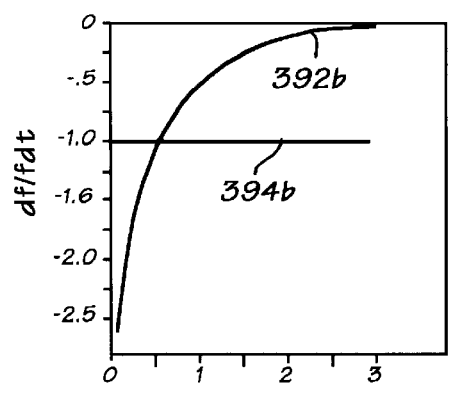

The signal generator of FIG. 20A was tested on a volunteer female patient, and was found to be highly effective both in relieving pain and, apparently, in accelerating healing. The patient suffered leg and elbow fractures in an automobile accident. The leg fracture was simple, and was treated conventionally with a cast. The elbow injury was much more severe, with multiple bone fractures and torn ligaments. After these fractures were fixed surgically using metal screws, the arm was put in a hinged brace to permit motion lest the joint "freeze." Healing time was projected at between six and eight weeks before the cast and brace could be removed.

The patient used the signal generator exclusively on the elbow fracture, for approximately 24 hours per day. She reported an almost immediate, dramatic reduction in pain, stating that use of the circuit was worthwhile for pain relief alone. After four weeks of treatment, the patient reported a sudden onset "different feeling" to the injured elbow, accompanied by a further reduction in pain. X-rays a week later confirmed that the elbow fracture had healed, and the brace was removed. At the same time, the leg fracture (which had received only conventional treatment) was also pronounced healed, and the cast was removed. Four months afterwards, the elbow was fully healed and the patient was undergoing physical therapy to restore the full normal range of motion. Eight months after removal of the cast, the patient appeared to have made a full recovery.

Additional embodiments of the present invention relate to the antibiotic and tissue-regenerating properties of electrically-generated silver ions described in U.S. Pat. No. 5,814,094 entitled "Iontophoretic System for Stimulation of Tissue Healing and Regeneration" and other publications. Zinc is another metal with beneficial properties. For example, supplemental zinc has been shown to be of value in overcoming herpes-virus outbreaks, including oral and genital herpes, chicken pox and shingles; topical zinc applications can also help heal specific localized lesions caused by these disorders, provided that adequate penetration of the zinc ion is achieved. A zinc-bearing electrode, for example a TENS-like pad in which the conductive gel contained a soluble zinc compound, could help to heal such lesions by driving in positive zinc ions. Similarly, any antibiotic or other drug having a water-soluble ionic form could be used with much the same sort of electrode, provided that the correct electrode polarity was chosen.

Figure 21:
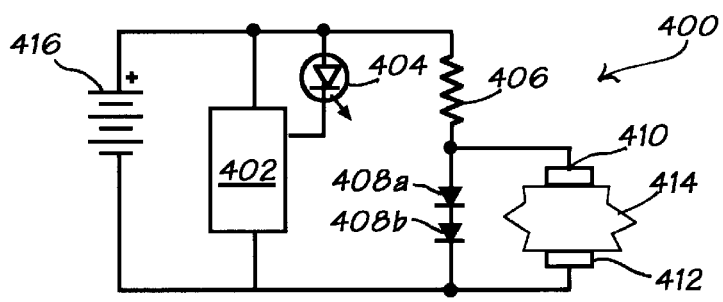
FIG. 21 is a circuit diagram of a typical silver ion generator.

A typical silver ion generator 400 is shown in FIG. 21. Power is furnished by a nine-volt battery 416. A integrated circuit 402 drives a flashing light-emitting diode 404 to verify operation and battery status. Battery current flows successively through a 200,000-ohm resistor 406 and two forward-biased silicon diodes 408a and 408b. A silver electrode 410 is connected to the anode end of the diode pair, and a counterelectrode 412 to the cathode end. Thus, the maximum electrode current is limited to about 40 microamperes (representing about 1.5 micromoles or 160 micrograms of $Ag^+$ generated per hour) and the maximum electrode voltage to two forward diode drops, or about 1.3 volts, at no load. With current flowing through a body part or tissue (represented by 414), the voltage is somewhat less and is controlled principally by surface ionization, silver-ion mobility and space-charge effects surrounding the electrodes.

A DC stimulus is not always desirable, since bone grows near the cathode (negative electrode) but often dies away near the anode (positive electrode). This phenomenon is believed to be due to electrolytic effects, which can cause tissue damage or cell death through pH changes and/or the dissolution of toxic metals into body fluids. The same effects can also kill or injure other types of cells and tissues near the anode. For this reason, many earlier devices for biomedical applications (including that described in U.S. Pat. No. 5,217,009) have relied solely on AC effects, screening out any net DC current from the outputs by passing the signal through one or more blocking capacitors. Even though many patients would benefit from the combination of AC or pulse stimuli (to further bone growth) and DC stimuli (for iontophoresis), no known devices provide this capability in a simple, user-programmable unit. Indeed, metal ion generators such as that of FIG. 21 cannot be used in combination with such an AC waveform generator, since diodes 408a, 408b would short out the positive portion of the waveform.

Figure 22:
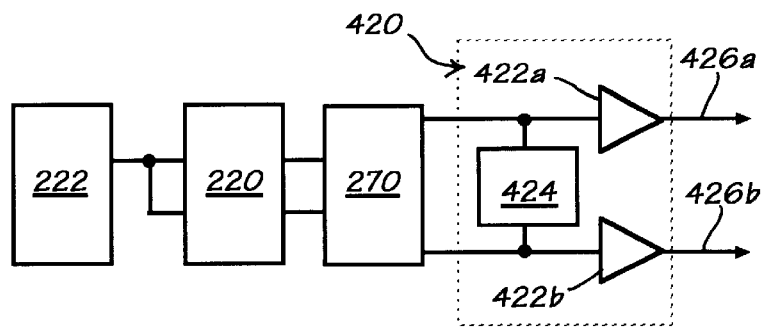
FIGS. 22–26 are circuit diagrams of DC signal generators according to the present invention.

This problem is eliminated by combining any of the circuits of FIGS. 22≧27 with an AC pulse generator according to the present invention. The resulting devices can be used to carry out iontophoresis at the same time as other electrotherapeutic treatment, with the same set of electrodes, and without significantly distorting AC signals passing through the same electrodes. Any of the following circuits may be used as a final output block in combination with any of the above-described AC signal generators, provided that both output lines from circuit block 270 have capacitive DC blocking (for example, as shown in FIG. 13 using capacitors 154a and 154b). The blocking capacitors are preferably nonpolarized, for example, monolithic ceramic units are suitable for use with the invention.

An idealized electrophoretic output circuit block 420 according to the present invention is shown in FIG. 22. Two voltage sources 422a and 422b are capacitively driven by, for example, the outputs of blocks 222, 220 and 270 (as in any of the previously described embodiments), and in addition are given a DC bias by a network 424 made up of resistors and (optionally) of other components such as diodes. As a result, the steady-state differential voltage between outputs 426a and 426b is set at an appropriate DC level for conducting electrophoresis—for example, approximately 0.9–1.3 volts—while superimposing on this voltage, without significant distortion, any AC. signals coming from block 270.

Figure 23:
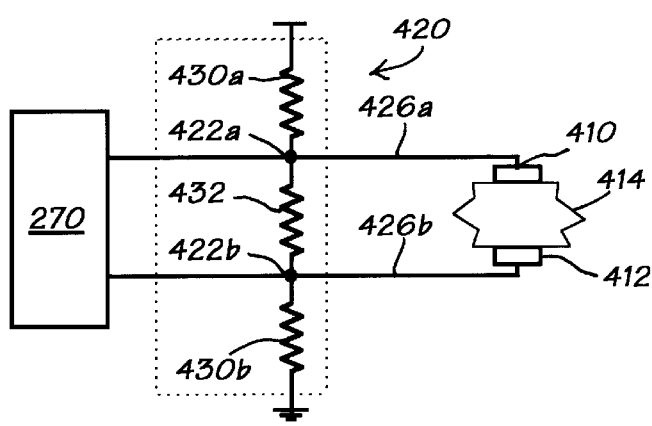

FIGS. 23–26 show examples of specific embodiments of block 420 (for clarity, circuit blocks or components prior to block 270 are not shown in these Figures). In the embodiment of FIG. 23, block 420 consists of a voltage-divider chain made up of resistors 430a, 430b and 432, so that voltage sources 422a and 422b are simply nodes in the chain. Resistors 430a and 430b are preferably relatively large and about equal in value, so that modest-sized capacitors can be used in block 270 without sacrificing AC performance. The value of resistor 432 is smaller and is chosen, relative to resistors 430a and 430b and the supply voltage, so that resistor 432 has a DC drop of about 1.3 volt.

In steady-state operation—for instance, during period $t_2$ of control oscillator 222 when VCO 220 is turned off, and after transient voltages have died away-no current enters or leaves block 420 from block 270, and outputs 426a and 426b carry steady DC potentials with a difference between them of about 1.3 volt. Electrophoresis thus takes place during most of $t_2$ as if no AC signal component were present.

During period $t_1$ of control oscillator 222, VCO 220 operates and current alternately enters and leaves through each of the connections between block 270 and nodes 422a and 422b. Since resistors 430a and 430b are of relatively high impedance, little of this current flows through the resistors; most of the current passes on to electrodes 410 and 412. Because resistor 432 is of a somewhat lower value and connected directly in parallel with electrodes 410, 412 and the tissue 414 which is to be treated, a significant amount of signal energy may be lost through the resistor, and thus the capacitors in block 270 may need to be somewhat larger than otherwise.

Figure 24:
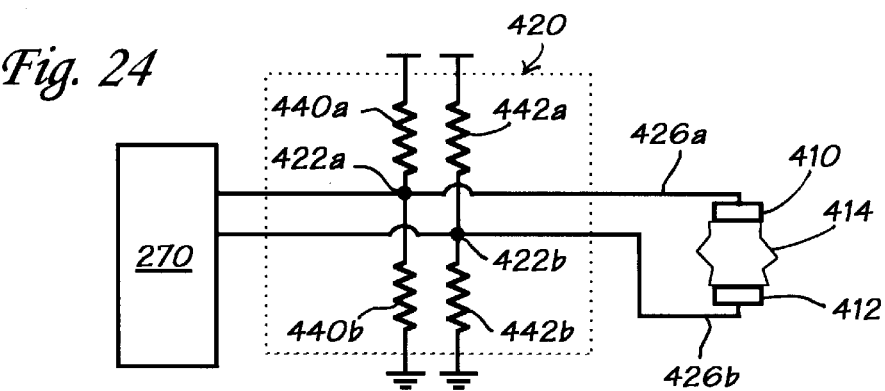

Alternatively, block 420 may include two parallel voltage dividers, each made up of two resistors with a central node (FIG. 24). In steady-state operation, resistors 440a and 440b set the voltage at node 422a at a first DC level, preferably close to one-half the supply voltage but about 0.6–0.7 volt above it, while resistors 442a and 442b set the voltage at node 422b about 1.3 volts lower than the voltage at node 422a. Resistors 440a, 440b, 442a, 442b preferably have values high enough that no significant part of the AC signal energy entering from block 270 is lost through the resistors, but low enough to permit adequate current to pass through for electrophoresis. As a result, during period $t_1$, AC signal treatment takes place as if block 420 were not present, while during most of period $t_2$ electrophoresis takes place as if the AC signal were not being applied. The optimum values for resistors 440a, 440b, 442a, 442b, and for other components of block 420, are best determined by a modest degree of experimentation in view of the intended application.

Electrophoresis requires a relatively constant applied voltage, with a current that varies with the amount of tissue to be treated (or, more properly, with the surface area of the electrode bearing the substance to be introduced, such as silver), it is deemed preferable to use relatively low-impedance voltage sources rather than the high-impedance sources possible with resistor chains. Hence, the last two embodiments of the invention consist of blocks 420 containing active voltagesourcing components to lower the source impedances.

Figure 25:
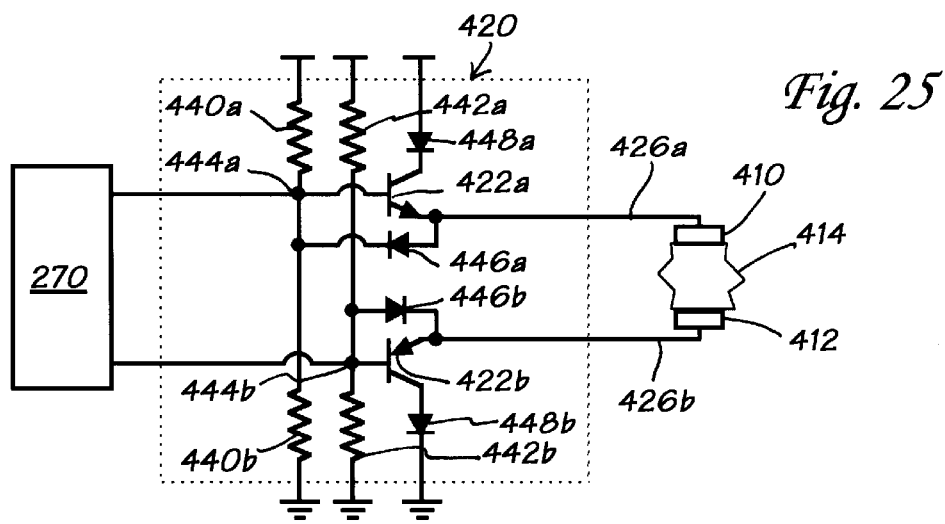

Another embodiment of block 420 is shown in FIG. 25, wherein resistors 440a, 440b, 442a and 442b in block 420 function as before, setting DC steady-state voltages of specific values on the nodes between them. Here, however, nodes 444a and 444b are set respectively about 1.3 volts above, and the same amount below, one-half the supply voltage. Each node 444a, 444b then feeds the base of a bipolar transistor, a PNP transistor in the case of node 444a and an NPN transistor in the case of node 444b. These transistors, connected as emitter followers, form voltage sources 422a and 422b.

In steady-state operation, transistor 422a sources current through its emitter to electrode 410, while transistor 422b sinks current from electrode 412, also through its emitter. Because of the voltage loss of about one forward diode drop (approximately 0.6–0.7 volt) between the base and emitter of a bipolar transistor, the resulting voltage difference between electrodes 410 and 412 is in the desired range of approximately 1.3 volts DC, but the impedance is lower by approximately the lesser of the current gains of the two transistors 422a, 422b.

Other types of active semiconductor devices can be substituted for transistors 422a and 422b, provided that the steady-state voltages at nodes 444a and 444b are adjusted to make up for the base-to-emitter or gate-to-source voltage drops of the selected devices to yield the desired DC output of approximately 0.9–1.3 volts DC. Suitable semiconductor devices for use with the invention include, but are not limited to, Darlington transistors connected as emitter followers, and junction field-effect transistors or MOS field-effect transistors connected as source followers.

For typical bipolar transistors (including but not limited to the 2N2222 (NPN) and 2N2907 (PNP)), current gains are in the range of 300:1, and thus about 300 times the previous treatment current is available, if needed, for treating large-area wounds or other major injuries. This current is drawn only if needed, rather than continuously as in the two preceding embodiments: under no load conditions, the battery drain due to block 420 consists only of the small amount of current flowing through the two resistor chains. Thus, the circuit of FIG. 25 maximizes efficiency and battery life while adding considerable flexibility in treatment.

During the generation of an AC signal by block 420, current alternately enters and leaves nodes 444a and 444b from block 270. When entering node 444a and leaving node 444b, the current passes through the base-emitter junctions of transistors 422a and 422b in the forward direction, and thus can be transferred at low impedance to the electrodes. Where the current enters node 444b and leaves node 444a, however, it cannot pass freely through these junctions in the reverse direction: without an alternate path, part of the AC signal waveform, and potentially some of its effectiveness, would be lost. Diodes 446a and 446b, connected antiparallel to the two base-emitter junctions, provide such a return path. Similarly, signal energy could be lost to the power supply through the base-collector junctions of bipolar transistors, or through the built-in diodes of most field-effect transistors, clipping and distorting especially those portions of the signal which lie outside the supply voltage range. Diodes 448a and 448b, inserted between devices 422b and 422b and the corresponding power-supply rails, prevent such losses.

Figure 26:
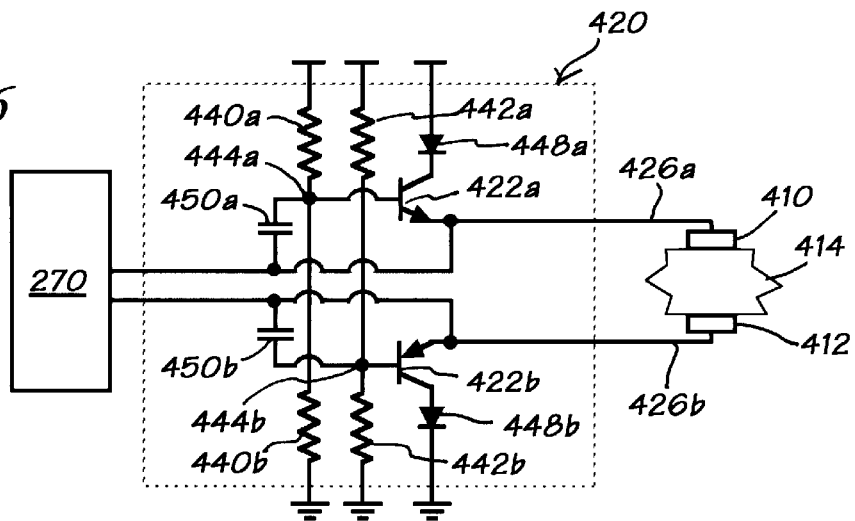

Another embodiment of block 420, wherein the DC output signal is stabilized more rapidly after an AC pulse than in the circuit of FIG. 25, is shown in FIG. 26. Here, the AC current from block 270 is applied to the output side, rather than the input side, of each of devices 422a, 422b and passes directly to outputs 426a, 426b and to the electrodes connected thereto. (While devices 422a and 422b are shown here as bipolar transistors, other suitable active semiconductor devices could be used instead.) Loss of signal energy through devices 422a and 422b, and possible damage to these devices from low-impedance signals applied to their outputs, is prevented by "bootstrapping" the outputs back to their inputs using small added capacitors 450a and 450b, respectively. This creates an AC short-circuit between these points, effectively turning off devices 422a and 422b to the AC part of the signal, while simultaneously preventing any interference with the DC functioning of the circuit. Diodes 448a and 448b function as described above.

Figure 27:
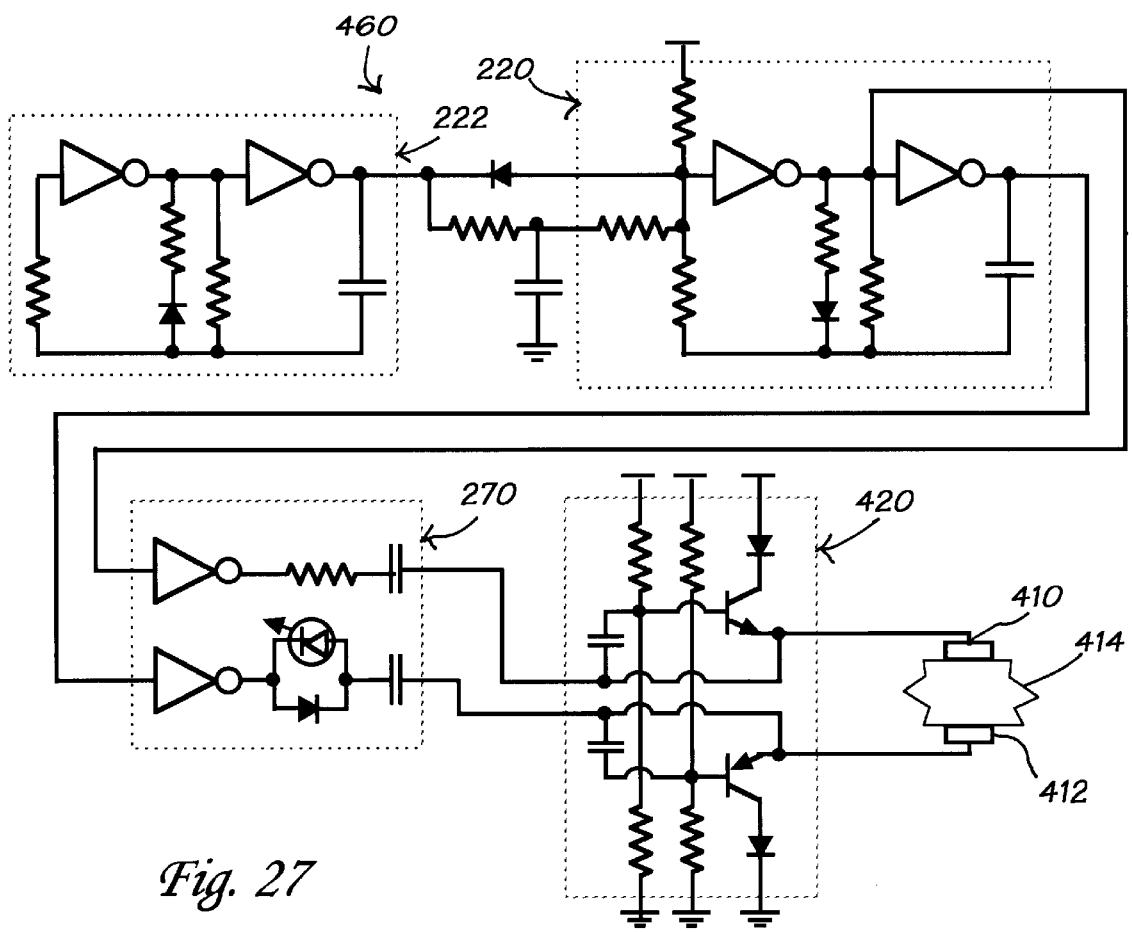
FIG. 27 is a circuit diagram of a signal generator for delivery of combined AC and DC signals according to the invention.

FIG. 27 shows another preferred embodiment of the present invention, in the form of a signal generator 460 which provides both AC and DC outputs. Signal generator 460 includes a control oscillator 222 and a VCO 220 connected as shown in FIG. 15A, an AC output buffering and DC blocking section 270 with nonpolarized capacitors as shown in FIG. 13, and the electrophoresis signal generator of FIG. 26 (for clarity, the individual components are not labeled). Signal generator 460 is preferably manufactured in the form of a printed circuit board with associated components. Thus, the generator (with a miniature 9-volt or other suitable battery) readily fits within a relatively small housing, such as a 1.5" by 2.25" by 0.75" plastic enclosure. If desired, other suitable components can be used instead of blocks 200, 220, 270.

In any of the above-described embodiments of the invention, output lines 426a and 426b (or their equivalents) preferably consist of a two-conductor, "zip cord" style cable made using rope-lay or "Litz" type cable, each such conductor consisting of numerous very fine wires twisted or braided together so as to be very resistant to metal fatigue. This type of cable minimizes the tendency to breakage which has been found in conductors consisting of a small number of strands, such as speaker wire. The preferred conductors may terminate either in "tip" style (approximately two-millimeter diameter pins), or in any other fashion which is compatible with the electrodes to be used with the signal generator.

Additional components may be added to the above-described signal generator without departing from the spirit of the present invention. Audible or tactile indicators may be useful to some persons (it should be noted that LED 160 functions as a visible "on-off" and low-battery indicator). The output waveform may be monitored by any convenient means, with an associated warning signal to alert the user when the waveform characteristics (frequency, pulse interval, magnitude, etc.) deviate from the selected characteristics by some predetermined amount. Such a warning signal could be used, for example, to alert the user to the need to change the batteries that power the generator. While DC power supplied by batteries is preferred, the generator may, if desired, include an AC adapter so that it can be operated by line current.

As noted above, a pulsed signal generator according to the present invention may have an adjustable output waveform; however, medical professionals may prefer a generator having a fixed output, or an output that is adjustable only in magnitude, for outpatient use. It will be apparent that the output waveform can be adjusted by any of a variety of techniques. By way of example, the generator may include any or all of the following: a potentiometer for adjusting the output amplitude; a switch for adjusting the polarity; a dial or keypad for selecting one of a plurality of available outputs; individual controls for adjusting the output pulse frequency, duration, and duty cycle. If desired, the generator may include a user-programmable microprocessor for adjusting any or all of these signal characteristics.

In most of the above-described specific embodiments of the present invention, the generator has complementary outputs (that is, the output waveform at one of the outputs is approximately equal to that at the other but of opposite polarity). Complementary outputs double the effective output voltage of the generator: a higher voltage not only yields greater flexibility in treatment options, but more easily permits a "swamping" resistor (such as resistor 156 in FIG. 13) to be added in series with the output in order to minimize the effects of the resistance of intact skin.

A pulsed signal generator according to the present invention makes use of simple, readily-available, generally inexpensive components to provide a rugged, reliable unit that may be tailored for a variety of biomedical applications. As will now be evident, the components of the generator can be selected to provide a device having an adjustable output (that is, adjustable in magnitude, polarity, frequency, or any combination of these factors), or a device that is specifically geared to a particular application, including but not limited to stimulation of fracture healing, TENS, osteoporosis treatment, etc.

With respect to the above description of the invention, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing description is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Thus, it will be apparent to those skilled in the art that many changes and substitutions can be made to the preferred embodiment herein described without departing from the spirit and scope of the present invention as defined by the appended claims.

What is claimed is:

1. A device for generating a pulsed electrical signal for use in biomedical applications, said device comprising:

first means for producing asymmetric oscillations, said first oscillator means producing a logic signal having first oscillations when said device is in electrical connection with a power source;

second means for producing asymmetric oscillations, said second oscillator means producing second oscillations when said device is in electrical connection with a power source;

circuit means for combining said first and second oscillations to produce an output waveform, said circuit means operating to switch said second oscillator "on" or "off" depending on a state of said logic signal;

output means for transmitting said output waveform to electrodes for stimulating biological tissue; and means for adjusting a frequency of said output waveform, said frequency-adjusting means electrically connected to said output means, said frequency-adjusting means varying said frequency in approximately logarithmic fashion.

2. The device as recited in claim 1, wherein said first oscillator means further comprises means for generating a first series of electrical pulses, each pulse of said first series having a first amplitude, a first width, and a first frequency, and wherein said second oscillator means further comprises means for generating a second series of electrical pulses, each pulse of said second series having a second amplitude, a second width, and a second frequency.

3. The device as recited in claim 1, wherein said first oscillator means further comprises means for generating a first series of electrical pulses, each pulse of said first series having a first amplitude, a first width, and a first frequency, wherein said second oscillator means further comprises means for generating a second series of electrical pulses, each pulse of said second series having a second amplitude, a second width, and a second frequency, and wherein said second frequency is higher than said first frequency.

4. The device as recited in claim 1, further comprising means for adjusting a frequency of said output waveform, said frequency-adjusting means electrically connected to said output means.

5. The device as recited in claim 1, wherein said output waveform is a pulse train having a pulse interval, further comprising means for adjusting said pulse interval, said interval-adjusting means electrically connected to said output means.

6. The device as recited in claim 1, further comprising means for adding a DC signal to said output waveform.

7. The device as recited in claim 1, wherein said output waveform has preselected characteristics, further comprising means in electrical connection with said output means for monitoring said output waveform, said monitoring means providing a warning signal if said output waveform deviates from said preselected characteristics.

8. The device as recited in claim 1, wherein said output waveform has a first magnitude and a first polarity, further comprising means for producing a next output waveform complementary to said output waveform, said next output waveform having a second magnitude approximately equal to said first magnitude and a second polarity opposite to said first polarity.

9. The device as recited in claim 1, wherein at least one of said first and said second oscillator means further comprises:

first signal-inverting means;

second signal-inverting means, said second signal-inverting means having an input driven by an output of said first signal-inverting means;

asymmetric resistive means coupling said output of said first signal-inverting means to a signal node;

capacitor means coupling an output of said second signal-inverting means to said signal node; and resistor means coupling said signal node to an input of said first signal-inverting means.

10. A device for generating a pulsed electrical signal for use in biomedical applications, said device comprising:

a first asymmetric oscillator, said first oscillator producing a first output signal having a first frequency when said device is in electrical connection with a power source;

a second asymmetric oscillator, said second oscillator producing a second output signal having a second frequency when said device is in electrical connection with said power source, said second frequency being higher than said first frequency, at least one of said first and second oscillators including a first signal inverter having an output, a second signal inverter having an input driven by said output of said first signal inverter, an asymmetric resistive circuit coupling said output of said first signal inverter to an isolated signal node, at least one capacitor coupling an output of said second signal inverter to said isolated signal node, and at least one resistor coupling said isolated signal node to an input of said first signal inverter;

means for combining said first and second output signals to produce an AC waveform;

means for adding a selected DC bias voltage to said AC waveform to produce an output waveform, and means for transmitting said output waveform to electrodes for stimulating biological tissue.

11. The device as recited in claim 10, further comprising means for varying a frequency of said output waveform.

12. The device as recited in claim 10, further comprising means for varying a frequency of said output waveform, said frequency-varying means varying said frequency in approximately logarithmic fashion.

13. The device as recited in claim 10, further comprising means for varying at least one of said first frequency and said second frequency in approximately logarithmic fashion.

14. The device as recited in claim 10, wherein at least one of said first and said second signal inverters in said first oscillator includes means for controlling operation of said second oscillator.

15. The device as recited in claim 10, wherein each of said first and second oscillators includes a first signal inverter having an output, a second signal inverter having an input driven by said output of said first signal inverter, an asymmetric resistive circuit coupling said output of said first signal inverter to an isolated signal node, at least one capacitor coupling an output of said second signal inverter to said isolated signal node, and at least one resistor coupling said isolated signal node to an input of said first signal inverter, and wherein said output of said first oscillator is a logic signal, said logic signal being applied to an input of at least one of said first and said second signal inverters of said second oscillator, said logic signal acting to switch said second oscillator "on" or "off" depending upon a state of said logic signal.

16. The device as recited in claim 10, wherein said asymmetric resistive circuit further comprises at least one resistor and at least one diode.

17. The device as recited in claim 10, further comprising means for adjusting a selected characteristic of said output waveform, said adjusting means including at least one component selected from the group consisting of adjustable components and switchable components.

18. The device as recited in claim 10, further comprising means for adding a DC signal to said output waveform.

19. The device as recited in claim 10, further comprising indicator means in electrical connection with said output means, said indicator means providing an indication of an operational state of said device, said indicator means being selected from the group consisting of optical indicators, audible indicators, and tactile indicators.

20. A device for generating a pulsed electrical signal for use in biomedical applications, said device comprising:

first means for producing asymmetric oscillations, said first oscillator means producing a logic signal having first oscillations when said device is in electrical connection with a power source;

second means for producing asymmetric oscillations, said second oscillator means producing second oscillations when said device is in electrical connection with a power source;

circuit means for combining said first and second oscillations to produce an output waveform, said circuit means operating to switch said second oscillator "on" or "off" depending on a state of said logic signal;

output means for transmitting said output waveform to electrodes for stimulating biological tissue; and means for adding a DC signal to said output waveform.

21. The device as recited in claim 20, wherein said first oscillator means further comprises means for generating a first series of electrical pulses, each pulse of said first series having a first amplitude, a first width, and a first frequency, and wherein said second oscillator means further comprises means for generating a second series of electrical pulses, each pulse of said second series having a second amplitude, a second width, and a second frequency.

22. The device as recited in claim 20, wherein said first oscillator means further comprises means for generating a first series of electrical pulses, each pulse of said first series having a first amplitude, a first width, and a first frequency, wherein said second oscillator means further comprises means for generating a second series of electrical pulses, each pulse of said second series having a second amplitude, a second width, and a second frequency, and wherein said second frequency is higher than said first frequency.

23. The device as recited in claim 20, further comprising means for adjusting a frequency of said output waveform, said frequency-adjusting means electrically connected to said output means.

24. The device as recited in claim 20, further comprising means for adjusting a frequency of said output waveform, said frequency-adjusting means electrically connected to said output means, said frequency-adjusting means varying said frequency in approximately logarithmic fashion.

25. The device as recited in claim 20, wherein said output waveform is a pulse train having a pulse interval, further comprising means for adjusting said pulse interval, said interval-adjusting means electrically connected to said output means.

26. The device as recited in claim 20, wherein said output waveform has preselected characteristics, further comprising means in electrical connection with said output means for monitoring said output waveform, said monitoring means providing a warning signal if said output waveform deviates from said preselected characteristics.

27. The device as recited in claim 20, wherein said output waveform has a first magnitude and a first polarity, further comprising means for producing a next output waveform complementary to said output waveform, said next output waveform having a second magnitude approximately equal to said first magnitude and a second polarity opposite to said first polarity.

28. The device as recited in claim 20, wherein at least one of said first and said second oscillator means further comprises:

first signal-inverting means;

second signal-inverting means, said second signal-inverting means having an input driven by an output of said first signal-inverting means;

asymmetric resistive means coupling said output of said first signal-inverting means to a signal node;

capacitor means coupling an output of said second signal-inverting means to said signal node; and resistor means coupling said signal node to an input of said first signal-inverting means.

* * * * *